United States Patent [19]

Patel et al.

[11] Patent Number: 4,828,603

[45] Date of Patent: May 9, 1989

[54] HERBICIDAL OXATRICYCLO-NONANE ETHERS

[75] Inventors: Kanu M. Patel, Wilmington, Del.; James E. Powell, Rising Sun, Md.

[73] Assignee: E. I. Du Pont de Nemours and Company, Wilmington, Del.

[21] Appl. No.: 171,029

[22] Filed: Mar. 21, 1988

[51] Int. Cl.[4] .................... A01N 43/90; C07D 493/18
[52] U.S. Cl. .......................................... 71/88; 71/90; 71/91; 71/92; 71/93; 71/94; 544/216; 544/335; 544/336; 546/270; 548/203; 548/204; 548/235; 548/236; 548/247; 548/262; 548/336; 548/374; 548/430; 548/431; 548/526
[58] Field of Search ..................... 549/46, 60, 44, 216, 549/300, 414, 459; 544/216, 335, 336; 546/270; 548/203, 204, 235, 236, 247, 262, 336, 374, 430, 431, 526; 71/88, 90, 91, 92, 93, 94

[56] References Cited

U.S. PATENT DOCUMENTS

| | | | |
|---|---|---|---|
| 4,486,220 | 12/1984 | Payne | 549/459 |
| 4,525,203 | 6/1985 | Payne et al. | 71/88 |
| 4,567,283 | 1/1986 | Payne et al. | 549/546 |
| 4,670,041 | 6/1987 | Payne et al. | 71/92 |

FOREIGN PATENT DOCUMENTS 243184 4/1987 European Pat. Off. .
2188931 4/1987 United Kingdom .

OTHER PUBLICATIONS

Viera et al., *Helvetica Chimica Acta*, 65(6): 1700–06, (1982).
Viera et al., *Helvetica Chimica Acta*, 66(6): 1865–71, (1983).
Black et al., *Helvetica Chimica Acta*, 67: 1612–15, (1984).
*J. Amer. Chem. Soc. Perkin Tans. I*, 903–906, (1985).
*J. Amer. Chem. Soc.*, vol. 5, 4115–4125, (1962).
*Aust. J. Chem.*, vol. 36, 2473–2482, (1983).

Primary Examiner—Mary C. Lee
Assistant Examiner—Bernard J. Dentz

[57] ABSTRACT

The present invention relates to novel tricyclo ether derivative compounds, to compositions containing these ether derivative compounds, and to methods of using these compounds or compositions to control the growth of undesired vegetation.

31 Claims, No Drawings

HERBICIDAL OXATRICYCLO-NONANE ETHERS

TECHNICAL FIELD

The present invention relates to novel tricyclo ether derivative compounds, to compositions containing these ether derivative compounds, and to methods of using these compounds or compositions to control the growth of undesired vegetation.

BACKGROUND OF THE INVENTION

Vieira et al., Helvetica Chimica Acta, 65(6) (1982), pp. 1700-06, teach the preparation of the oxabicyclic cyanohydrin acetates

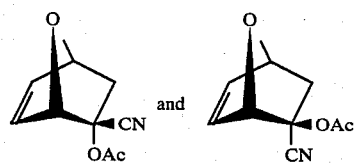

via a Diels-Alder reaction. In addition, the publication discloses epoxidation of the above compounds with m-chloroperbenzoic acid to yield

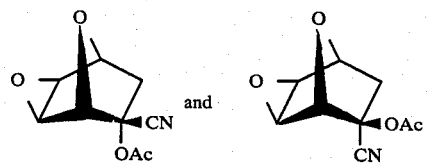

as well as the hydrolysis of such compounds to yield

Vieria et al., Helvetica Chimica Acta, 66(6) (1983), pp. 1865-71 teach a chiral variant of the above described reaction which produces oxabicyclic cyanohydrin esters homologous to those depicted above, but with a (—)-camphanoyl group instead of an acetate group.

Black et al., Helvetica Chimica Acta, 67 (1984), pp. 1612-15, disclose a method for the preparation of the chiral oxabicyclic ketone

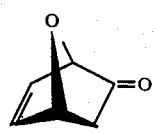

via diastereoselective formation of a brucine complex of the corresponding cyanohydrin acetate.

Payne et al., U.S. Pat. No. 4,567,283 and Payne et al., U.S. Pat. No. 4,670,041 disclose a variety of herbicidal bicyclic ethers of the Formula

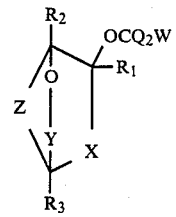

wherein X is $(-CR_4R_4-)_m$ in which m is 0 or 1; Y is $(-CR_5R_6-)_n$ in which n is 0, 1 or 2; Z is $(-CR_7R_7-)_p$ in which p is 1, 2 or 3; the sum of m+n+p is an integer of 2 to 5, inclusive; $R_2$ and $R_3$ each is H or alkyl, and the like; $R_1$ is H or alkyl; both of Q are H or F atoms; and W is an unsaturated, aromtic or heterocyclic group. This reference also disclosed certain bicyclic and monocyclic intermediates to these compounds.

Payne et al., U.S. Pat. No. 4,525,203, disclose herbicidal bicyclic ethers of the Formula

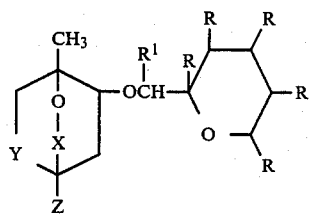

wherein X is a single bond or $-C(CH_3)_2$; Y is a single bond or $-CH_2-$ with the proviso that both X and Y are not a single bond, and Z is H or alkyl; each R is H, hydroxy, oxo, methylene, alkyl or alkoxy, or one pair of adjacent R groups form a carbon-carbon bond; and $R^1$ is H or alkyl. This patent also discloses certain bicyclic and monocyclic intermediates to these compounds.

GB No. 2188-931 discloses compounds of the following formula as herbicides:

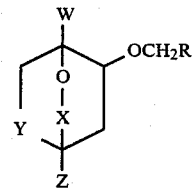

wherein
W and X is O or $CH_2$;
Y is C—C bond, O, $CH_2$, $CH_2CH_3$ or CHR;
Z is C—C bond, O, $CH_2$, $CH_2CH_3$. provided W, X, Y and Z are not adjacent O or $C_2H_4$.

J. Chem Soc. Perkin Trans. I, 903-906 (1985), J. Amer. Chem. Soc., Vol. 84, 4115-4125 (1962) and Aust. J. Chem., Vol. 36, 2473-2482 (1983), disclose intermediates such as I, II and III, respectively, useful for the preparation of the compounds of the invention.

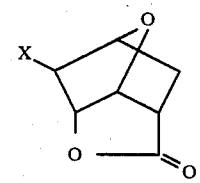

I

-continued

X = Br or OH

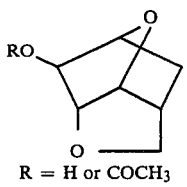

R = H or COCH₃

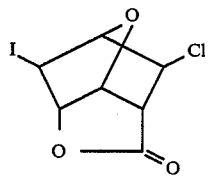

SUMMARY OF THE INVENTION

This invention pertains to compounds of Formula I including steriosomers, suitable agricultural compositions containing them and their use as broad spectrum preemergent and postemergent herbicides.

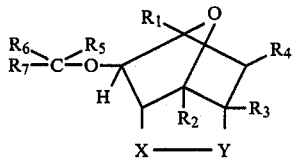 (I)

wherein,

X is O, S, NR' or CR'R';
Y is CR"R", C(O), S(O)$_n$ or P(O)(OR$_a$); n is 1 or 2;
R$_1$ is H or a straight-chain C$_1$—C$_3$ alkyl;
R$_2$ is H, C$_1$—C$_6$ alkyl, C$_2$—C$_4$ alkenyl, C$_2$—C$_4$ alkynyl, phenyl or C$_1$—C$_4$ alkyl substituted by phenyl, OH, CN, OR$_a$, SO$_2$R$_a$, phenyl-SO$_2$, N$_3$, CO$_2$R$_a$, CO$_2$H, OP-(O)(OR$_a$)$_2$, P(O)(OR$_a$)$_2$, OC(O)N(R$_a$)$_2$, OC(O)NHR$_a$ or OC(S)N(R$_a$)$_2$;
R$_3$ is H, C$_1$—C$_3$ alkyl, CN, CO$_2$R$_a$, C(O)N(R$_a$)$_2$, C(O)NHR$_a$, C(O)R$_a$, P(O)(OR$_a$)$_2$, CH$_2$OH, CH$_2$OR$_a$, CH$_2$SR$_a$, CH$_2$CN or Cl;
R$_4$ is H, NO$_2$, CO$_2$R$_a$, C(O)NHR$_a$, C(O)NHR$_a$, C(O)N(R$_a$)$_2$, CN or OR$_a$;
R$_5$ is H or F;
R$_6$ is H, F or CH$_3$;
R$_7$ is phenyl optionally substituted with 1-3 substituents selected from W, or J optionally substituted with 1-2 substituents selected from W';

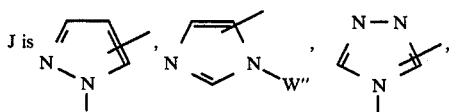

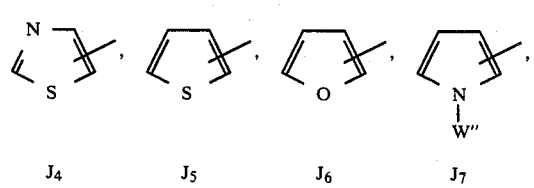

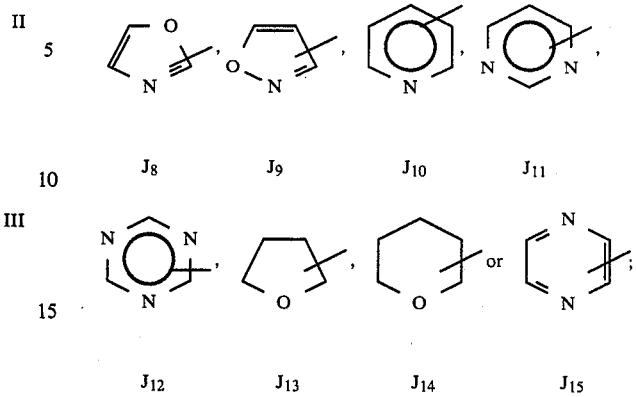

R' is H, C$_1$—C$_3$ alkyl or phenyl;
R" is H or C$_1$—C$_3$ alkyl;
R$_a$ is C$_1$—C$_3$ alkyl;
W is Cl, F, Br, OH, CN, C$_1$—C$_3$ alkyl, C$_1$—C$_3$ haloalkyl, C$_2$—C$_3$ alkenyl, C$_2$—C$_3$ alkynyl, NH$_2$, C(O)NH$_2$, OR$_a$, SR$_a$, NR$_a$H, NR$_a$R$_a$, SOR$_a$, SO$_2$R$_a$, C(O)R$_a$ or CO$_2$R";
W' is C$_1$—C$_3$ alkyl, F, Cl, Br, C$_1$—C$_2$ alkoxy or C$_1$—C$_2$ alkylthio; and
W" is H or C$_1$—C$_3$ alkyl; provided that when n is 1 then X is CR'R'.

Preferred Embodiments

Preferred for either their biological activity or ease of synthesis are:

1. Compounds of Formula I wherein
R$_7$ is phenyl optionally substituted with 1-2 substituents selected from Cl, F, C$_1$—C$_3$ alkyl, OR$_a$, C$_1$—C$_3$ haloalkyl, SR$_a$, C$_2$—C$_3$ alkenyl or C$_2$—C$_3$ alkynyl or J optionally substituted with 1-2 substituents selected from C$_1$—C$_2$ alkyl, F, Cl, or OCH$_3$.
2. Compounds of Preferred 1 wherein
R$_1$ is H or C$_1$—C$_2$ alkyl;
R$_2$ is H, C$_1$—C$_2$ alkyl, C$_2$—C$_3$ alkenyl or propargyl; and
R$_3$ is H or C$_1$—C$_2$ alkyl.
3. Compounds of Preferred 2 wherein
X is O; and
Y is CR"R".
4. Compounds of Preferred 2 wherein
X is O; and
Y is C(O).
5. Compounds of Preferred 2 wherein
X is O; and
Y is SO$_2$.
6. Compounds of Preferred 2 wherein
X is O; and
Y is P(O)(OR$_a$).
7. Compounds of Preferred 2 wherein
X is CR'R'; and
Y is CR"R".
8. Compounds of Preferred 2 wherein
X is CR'R'; and
Y is C(O).
9. Compounds of Preferred 2 wherein
X is CR'R'; and
Y is SO or SO$_2$.
10. Compounds of Preferred 2 wherein
X is CR'R'; and Y is P(O)(OR$_a$).
11. Compounds of Preferred 2 wherein
X is NR'; and
Y is CR"R".
12. Compounds of Preferred 2 wherein
X is NR'; and
Y is C(O).
13. Compounds of Preferred 2 wherein
X is NR'; and
Y is SO$_2$.
14. Compounds of Preferred 2 wherein
X is NR'; and
Y is P(O)(OR$_a$).
15. Compounds of Preferred 2 wherein
X is S; and
Y is CR"R".
16. Compounds of Preferred 2 wherein
X is S; and
Y is C(O).
17. Compounds of Preferred 2 wherein
X is S; and
Y is SO$_2$.
18. Compounds of Preferred 2 wherein
X is S; and
Y is P(O)(OR$_a$).
Specifically preferred are:
4,8-dioxatricyclo(4.2.1.0$^{3,7}$)nonane-1,5,5,7-tetramethyl-2-(phenylmethoxy), (1RS, 2RS).
4,8-dioxatricyclo(4.2.1.0$^{3,7}$)nonane-2-(2-fluorophenyl)methoxy)1,5,5,7-tetramethyl, (1RS, 2RS).

DETAILED DESCRIPTION OF THE INVENTION

Compounds of Formula I can be prepared from alcohols of Formula II and alkylating agents in the presence of a base and an inert solvent according to the well-known Williamson ether synthesis route (See N. Baggett in Comprehensive Organic Chemistry, D. Barton and W. D. Ollis eds., Vol. 1, pp. 819-832, Pergamon Press, N.Y. (1979)). Suitable alkylating agents are, for example, arylmethyl and heterocyclicylmethyl halides and sulfonate esters. Suitable bases are, for example, alkali metal hydrides, hydroxides, and alkoxides. Suitable inert solvents include tetrahydrofuran, 1,4-dioxane, dimethylformamide, N,N-dimethylacetamide, and dimethylsulfoxide. Alternatively, phase transfer type conditions can be employed in the Williamson ether synthesis as referenced above. A typical example of this etherification process is depicted in Scheme I.

Scheme I

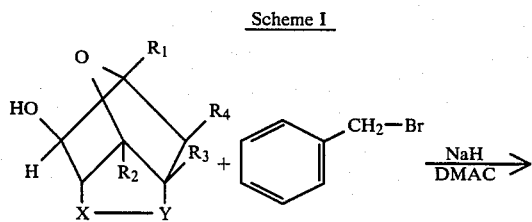

II

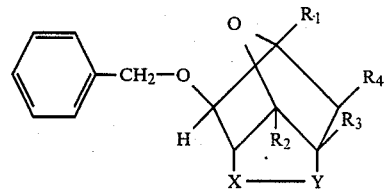

The alcohols of Formula II can be prepared through ring opening of a precursor epoxide of Formula III which in turn can be generated through epoxidation of a bicyclic olefin of Formula IV. The epoxide III may or may not be an isolated intermediate in the overall transformation of bicyclic olefin IV into tricyclic alcohol II depending on the nature of the functionally HX—Y and the specific epoxidation reaction conditions. Suitable epoxidation agents are, for example, peroxycarboxylic acids such as peroxyformic acid, peroxyacetic acid, 3-chloroperoxybenzoic acid and the like in solvents such as formic and acetic acids, methylene chloride, chloroform, diethyl ether, tetrahydrofuran, and benzene. Under circumstances where the thus formed epoxides are isolated, the subsequent ring opening reaction may be promoted under acidic or basic conditions depending on the nature of the substituent HX—Y. Suitable agents are, or example, strong mineral acids, carboxylic acids like acetic or formic acids, and sulfonic acids like toluenesulfonic acid or alkali metal hydrides such as potassium hydride, alkali metal hydroxides like sodium hydroxide, alkyl lithiums, and lithium amides such as lithium diisopropylamide. These reagents are employed in solvents and under conditions familiar to those skilled in the art. For example, where the functionality HX—Y is HO—CH$_2$, the use of sodium hydroxide in refluxing water is suitable or where the HX—Y functionality is HO—C(O), the use of a catalytic amount of p-toluenesulfonic acid in methylene chloride at 0°-40° C. is suitable. A typical transformation of bicyclic olefin IV into tricyclic alcohol II is outlined in Scheme II.

Scheme II

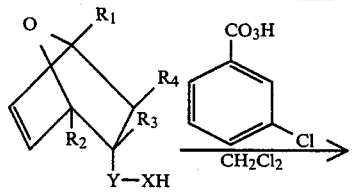

IV

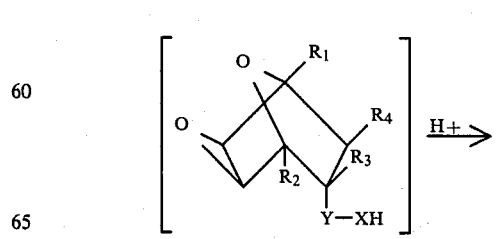

III

-continued
Scheme II

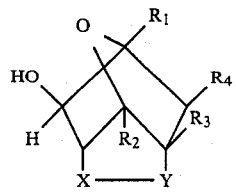

II

As outlined in Scheme III, bicyclic olefin of Formula IV may be obtained directly where Z=Y—XH or in many cases indirectly where Z≠Y—XH but rather a group capable of further transformation into the Y—XH functionality through a Diels Alder cycloaddition between a furan of Formula V and a functionalized olefin of Formula VI wherein Z corresponds to functional groups such as C(O)OR', C(O)CHR'R', S(O)$_n$OR', S(O)$_n$CHR'R', and P(O)(OR')$_2$. Furan Diels-Alder cycloaddition reactions are well documented in the literature. See, for example, K. A. Black and P. Vogel, *Helvetica Chemica Acta,* 67, 1612 (1984); M. P. Kuntsmann, D. S. Tarbell, and R. L. Autrgy, *J. American Chemical Society,* 84, 4115 (1962); F. Brion, *Tetrahedron Letters,* 23, 5299 (1982); T. A. Eggelte, H. de Koning, and H. O. Huisman, *Heterocycles,* 4, 19 (1976); U.S. Pat. No. 4,555,581; J. A. Moore and E. M. Partain III, *J. Organic Chemistry,* 48, 1105 (1983); P. F. Schuda and J. M. Bennett, *Tetrahedron Letters,* 23, 5525 (1982); N. Ono, A. Kamimura, and A. Kaji, *Tetrahedron Letters,* 27, 1595 (1986); L. L. Klein and T. M. Deeb, *Tetrahedron Letters,* 26, 3935 (1985); M. V. Sargent and F. M. Dean in *Comprehensive Heterocyclic Chemistry,* A. R. Katritzky and C. W. Rees, eds., Vol. 4, pp. 619-636, Pergamon Press, N.Y. (1984).

These furan cycloadditions are typically conducted at 0°-25° C. in the absence of solvent for periods of a few hours to seven days often in the presence of catalysts like aluminum chloride, boron trifluoride etherate, zinc iodide, or titanium tetrachloride. The cycloaddition reaction may afford isomeric mixtures which can be separated and purified by techniques such as chromatography, crystallization, and distillation familiar to those skilled in the art. Under circumstances (i.e., where Z≠Y—XH) where the functionality Z, for example Z=CO$_2$CH$_3$, in the Diels-Alder cycloadduct IVa is unsuitable for use in the epoxide-forming or epoxide-opening reactions shown in Scheme II, then this functionality may be transformed into the appropriate functionality Y—XH embodied in Formula IV through conventional reactions such as ester hydrolysis, carbonyl group reduction, and Grignard addition, all well-known to those skilled in the art. The furans V and functionalized olefins VI used as the starting points for this process often are commercially available or are known in the literature. See, for example, D. M. X. Donnelly and M. J. Meegan in *Comprehensive Heterocyclic Chemistry,* A. R. Katritzky and C. W. Rees, eds., Vol. 4, pp. 657-712, Pergamon Press, N.Y. (1984), and the references cited above on furan Diels-Alder reactions.

Scheme III

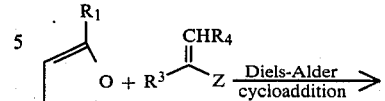

V       VI

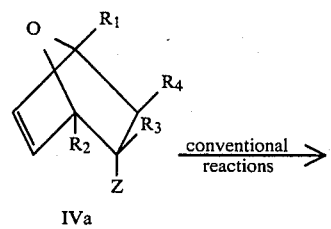

IVa

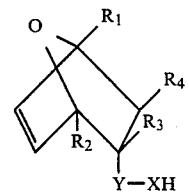

IV

The tricyclic alcohol of Formula II can also be obtained as outlined in Scheme IV from the Diels-Alder adduct of Formula IVa by an alternative reaction sequence. First, the adduct IVa is epoxidized to afford bicyclic epoxide IIIa as discussed for the conversion IV to III (Scheme II). Next, the functional group Z in epoxide IIIa is transformed into the functional group Y—XH in epoxide III as discussed for the conversion IVa to IV. Finally, the epoxide ring in Formula IIIa is opened by the internal functional group Y—XH to afford tricyclic alcohol II. Again, the intermediate III may or may not be isolated as dictated by the particular reaction conditions involved in the conversion of IIIa to III.

For example, the epoxide IIIa where Z=CO$_2$CH$_3$ may be hydrolyzed with lithium hydroxide in aqueous tetrahydrofuran at 0°-25° C. and then treated with concentrated hydrochloric acid until the pH reaches 1-2 in order to provide the tricyclic alcohol II where X—Y=O—C(O).

Scheme IV

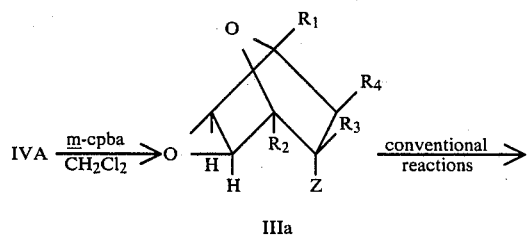

IIIa

-continued
Scheme IV

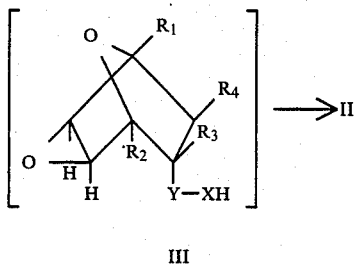

The following examples further illustrate preparation of the compounds of this invention.

EXAMPLE 1

Preparation of 2-((2-methylphenyl)methoxy)-1,5,5,7-tetramethyl-4,8-dioxatricyclo[4.2.1.0$^{3,7}$]nonane, (1RS, 2RS)

Step A: Methyl Endo-1,4-dimethyl-7-oxabicyclo(2.2.1)hept-5-ene-2-carboxylate.

2,5-Dimethylfuran was reacted with methyl acrylate in the presence of aluminum chloride according to U.S. Pat. No. 4,555,581, to provide an epimeric mixture of methyl 1,4-dimethyl-7-oxa-bicyclo(2.2.1)-hept-6-ene-2-carboxylates. Flash chromatography (silica gel; 3:1 hexane:ether) afforded in early fractions 1% of the exo-epimer and in latter fractions 5% of the title ester as a pale yellow liquid.

$^1$HNMR(CDCL$_3$, 200 MHz), δ 6.25 (d, J-6 Hz, 1H), 6.07 (d, J-6 Hz, 1H), 3.65 (s, 3H), 2.92 (d, d J=9, 5 Hz, 1H), 2.00 (d, d, J=13, 9 Hz, 1H), 1.83 (d, d, J=13, 5 Hz, 1H), 1.74 (s, 3H) 1.60 (s, 3H).

Step B: Methyl 1,4-Dimethyl-5,6-exo-epoxy-7-oxabicyclo(2.2.1)heptane-2-endo-carboxylate.

3-Chloroperoxybenzoic acid (9.03 g; 41.9 mmol of 80% technical) was added in portions at 11°–14° C. to a solution of the title ester of Step A (6.93 g; 38.1 mmol) in methylene chloride. After complete addition stirring was continued at room temperature for 3.5 hr before cooling in an ice-water bath for 0.5 hr. The reaction mixture was suction filtered and the collected solid was washed with additional chilled CH$_2$Cl$_2$ (2×25 ml). The combined filtrates were diluted with CH$_2$Cl$_2$ (50 ml), washed successively with 10% Na$_2$SO$_3$ (2×100 ml), saturated NaHCO$_3$ (2×100 ml), and saturated NaCl (100 ml), dried (MgSO$_4$), and rotatory evaporated to leave 7.24 g of a colorless oil. This oil was combined with identical material (9.14 g total) from a second run and purified by flash chromatography (silica gel; 1:1 ether:hexane) to afford 8.71 g (91%) of the title ester as a white solid, m.p. 45.5°–47.0° C.

NMR(CDCl$_3$, 200 MHz), δ 3.73 (s, 3H), 3.30 (d, J=3 Hz, 1H), 3.26 (d, J-3 Hz, 1H) 2.86 (d,d J=11, 5 Hz, 1H), 2.07 (d, d, J=13, 5 Hz, 1H), 1.88 (d, d, J=13, 11 Hz, 1H), 1.63 (s, 3H), 1.52 (s, 3H) IR(CH$_2$Cl$_2$) 1720 cm$^{-1}$; MS(SP/CI) 199 (M+1, 100%).

Step C: 1,5,5,7-Tetramethyl-4,8-dioxatricyclo[4.2.1.0$^{3,7}$]nonan-2-ol, (1RS, 2RS)

Using a cool water bath, a solution of the title ester of Step B (5.2 g; 26.2 mmol) in dry THF (30 ml) was added dropwise at 18°–28° C. over 0.5 hr to methylmagnesium bromide (22.0 ml; 66.0 mmol; 3M in ether) diluted with THF (25 ml). After complete addition, the reaction mixture was stirred at room temperature for 7 hr before being poured with stirring into a chilled mixture of methylene chloride (150 ml) and saturated aqueous ammonium chloride (150 ml). The phases were separated and the aqueous was extracted with additional CH$_2$Cl$_2$ (2×150 ml). The combined organic phases were washed with saturated salt solution (1×500 ml), dried (MgSO$_4$), and rotatory evaporated to leave 5.3 g of a colorless oil. Combination with other identical material (7.2 g total) and flash chromatography (silica gel; 9:1 ether:hexane) afforded 6.24 g (87%) of pure title alcohol as a white solid, m.p. 78°–80° C.

NMR(CDCl$_3$, 200 MHz), δ 3.67 (s, 1H), 3.53 (d, J=9 Hz, 1H), 2.1–1.8 (m, 3H), 1.74 (strong singlet overlapping a doublet, J=9 Hz, together 4H), 1.40 (s, 3H), 1.31 (s, 3H), 1.27 (s, 3H), IR(CH$_2$Cl$_2$) 3537, 3430 cm$^{-1}$; MS(SP/CI) 199 (M+1, 100%).

Step D: 2-((2-methylphenyl)methoxy)-1,5,5,7-tetramethyl-4,8-dioxatricyclo[4.2.1.0$^{3,7}$]nonane, (1RS, 2RS)

Sodium hydride (0.25 g; 6.25 mmol of a 60% oil dispersion) was washed by decantation with hexane and then suspended in dimethylformamide (3 ml). A solution of the title alcohol of Step C (0.99 g; 5.00 mmol) in DMF (5 ml) was added dropwise over 10 min at 22°–25° C. under N$_2$. The reaction mixture was then warmed at 35°–45° C. for 30 min until hydrogen evolution ceased. The reaction solution was cooled in an ice-water bath during the dropwise addition of a solution of 2-methylbenzyl bromide (1.02 g; 5.50 mmol) in DMF (8 ml) at 5°–10° C. over 30 min. The reaction solution was stirred 1 hour further in the cold and then at room temperature. After 72 hr the reaction solution was poured into water (75 ml) and extracted with methylene chloride (3×75 ml). The combined organic extracts were washed with saturated salt solution (1×200 ml), dried (MgSO$_4$), and rotatory evaporated (ultimately at 50° C.) to leave 1.80 g of a yellow oil. Purification by flash chromatography (silica gel; 3:2 hexane-ether) provided 1.38 g (91%) of the title ether as a colorless oil.

NMR(CDCl$_3$, 200 MHz), δ 7.40–7.30 (m, 1H), 7.20–7.10 (m, 3H), 4.56 (AB quartet, J=12 Hz, 2H), 3.91 (s, 1H), 3.32 (s, 1H), 2.33 (s, 3H), 204 (d, d, J=10, 2 Hz, 1H), 1.88 (d, d, J=14, 2 Hz, 1H), 1.77 (strong singlet overlapping a multiplet, together 4H), 1.42 (s, 3H), 1.34 (s, 3H), 1.27 (s, 3H), IR(CH$_2$Cl$_2$) 1605 weak, 1490 weak cm$^{-1}$; MS (SP/CI) 303 (M+1, 3%).

EXAMPLE 2

Preparation of 2-((2-chloro-6-fluorophenyl)methoxy)-1,7-dimethyl-4,8-dioxatricyclo[4.2.1.0$^{3,7}$]nonane, (1RS, 2RS)

Step A: 1,7-Dimethyl-4,8-dioxatricyclo[4.2.1.0$^{3,7}$]nonan-2-ol, (1RS, 2RS)

A solution of the epoxyester from Example 1—Step B (5.70 g; 28.80 mmol) in dry tetrahydrofuran (45 ml, THF) was added dropwise over 45 min to a refluxing mixture of lithium aluminum hydride (0.80 g; 21.10 mmol) in THF (45 ml) under nitrogen. After refluxing for 3.5 hr further, the reaction mixture was cooled in an ice-water bath during the cautious sequential addition of 0.8 ml of water, 0.8 ml of 15% aqueous sodium hydorxide, and 0.8 ml of water. The grannula precipitate was removed by suction filtration and washed with additional THF (3×25 ml). The combined filtrates were rotatory evaporated to leave 4.44 g of the title alcohol as a colorless oil which crystalized upon standing, m.p. 37°–40° C.

NMR(CDCl₃, 300 MHz), δ 3.90 (d of d, J=8, 3 Hz, 1H), 3.82 (d, J=8 Hz, 1H), 3.64 (s, 1H), 3.53 (d, J=8 Hz, 1H, collapsed to a singlet on D₂O exchange), 2.20 (d, t, J=10, 3 Hz, 1H), 2.06 (d, d, J=12, 10 Hz, 1H), 2.04 (d, J=8 Hz, 1H) 1.58 (s, 3H), 1.52 (d, d, J=12, 3 Hz, 1H), 1.42 (s, 3H), IR(CH₂Cl₂) 3660, 3570, 3440 cm⁻¹; MS (SP/CI), 171 (M+1, 64%).

Step B: 2-((2-chloro-6-fluorophenyl)methoxy)-1,7-dimethyl-4,8-dioxatricyclo[4.2.1.0³,⁷]-nonane, (1RS, 2RS)

Under conditions analogous to those described in Example 1—Step D, the alcohol described in Step B above (1.06 g; 6.25 mmol) was alkylated with 2-chloro-6-fluorobenzyl chloride (1.23 g; 6.88 mmol) to provide after purification by flash chromatography (silica gel; 3:2 hexane-ether) 0.90 g (46%) of the title ether as a colorless oil.

NMR(CDCl₃, 200 MHz), δ 7.30–7.15 (m, 2H), 7.05–6.92 (m, 1H), 4.73 (doublet of AB quartet, J=12, 2 Hz, 2H), 3.92 (d, d, J=9, 5 Hz, 1H), 3.88 (s, 1H) 3.82 (d, J=9 Hz, 1H), 3.31 (s, 1H) 2.20 (m, 1H) 2.05 (d, J=12 Hz, 1H), 1.60 (s, 3H) 1.50 (d, d, J=12, 2 Hz, 1H), 1.40 (s, 3H), IR(CH₂Cl₂) 1610, 1580, 1455 cm⁻¹; MS (SP/CI) 313 (M+1, 1 Cl, 19%).

EXAMPLE 3

Preparation of 1,7-Dimethyl-2-hydroxy-4,8-dioxatricyclo[4.2.1.0³,⁷]nonan-5-one, (1RS, 2RS)

Step A: Endo-1,4-dimethyl-7-oxabicyclo(2.2.1)-hept-5-ene-2-carboxylic acid

Lithium hydroxide monohydrate (0.46 g; 11.0 mmol) was added in one portion to a solution of the ester prepared in Example 1—Step A (1.82 g; 10.0 mmol) in tetrahydrofuran (15 ml) and water (10 ml) stirring at 2° C. Stirring was continued at 2°–5° C. for 3.5 hr before the addition of more lithium hydroxide monohydrate (0.23 g; 5.50 mmol). After an additional 2.5 hr of stirring in the cold, the reaction solution was poured into ice-water (50 ml) and extracted with methylene chloride (50 ml, CH₂Cl₂, discarded). The aqueous phase was acidified to pH 2 with 1N HCl and then extracted with CH₂Cl₂ (4×50 ml). These combined organic extracts were washed with saturated salt solution (50 ml), dried (MgSO₄), and rotatory evaporated to provide 1.64 g (98%) of the title acid as a white solid, m.p. 67°–68° C.

NMR(CDCl₃, 300 MHz), δ 9.0 (very broad singlet, 1H), 6.28 (d, J=5 Hz, 1H), 6.14 (d, J-5 Hz, 1H), 2.96 (d, d, J-9, 4 Hz, 1H), 2.01 (d, d, J-12, 9 Hz, 1H), 1.82 (d, d, J=12, 4 Hz, 1H), 1.76 (s, 3H), 1.60 (s, 3H), IR(CH₂Cl₂) 3550-2300, 1710 cm⁻¹; MS (SP/CI) 169 (M+1, 17%).

Step B: 1,7-Dimethyl-2-hydroxy-4,8-dioxatricyclo[4.2.1.0³,⁷]nonan-5-one, (1RS, 2RS)

3-chloroperoxybenzoic acid (10.62 g; 49.20 mmol; 80% technical) was added in about 0.5 g portions over 15 min to a solution of the acid from Step A above (7.52 g; 44.80 mmol) in methylene chloride (80 ml), stirring at 0°–5° C. Stirring was continued in the cold for 4.5 hr and then at room temperature for 3 hr. The reaction mixture was recooled in an ice-water bath for 30 min and then suction filtered. The collected solid was washed with cold CH₂Cl₂ (2×25 ml). The combined filtrates were diluted with CH₂Cl₂ (100 ml) and washed successively with 10% aqueous sodium sulfite (1×200 ml, 1×100 ml), saturated aqueous sodium bicarbonate (1×200 ml, 1×100 ml), and saturated salt solution (150 ml). The combined aqueous washings were acidified to pH 1-2 with concentrated HCl and extracted with CH₂Cl₂ (4×200 ml). These latter, combined organic extracts were washed with saturated salt solution (3×200 ml), dried (MgSO₄), and rotatory evaporated to leave 8.34 g of a white solid, m.p. 134°–140° C. This material was purified further by flash chromatography (silica gel; ether) followed by crystallization (ether-hexane) to provide 3.49 g (42%) of the title hydroxylactone as a white solid, m.p. 95°–96.5° C.

NMR(CDCl₃, 300 MHz), δ 4.18 (d, J=1 Hz, 1H), 3.80 (d, J=5 Hz, 1H), 2.53 (d, d, d, J=11, 2.5, 1 Hz, 1H), 2.21 (d, d, J-13.5, 11 Hz, 1H), 2.15 (broad absorption, 1H), 2.00 (d, d, J=13.5, 2.5 Hz, 1H), 1.66 (s, 3H), 1.49 (s, 3H), IR(CH₂Cl₂) 3570, 3480, 1785 cm⁻¹; MS (SP/CI), 185 (M+1, 100%).

Step C: 1,7-Dimethyl-1-phenylmethoxy-4,8-dioxatricyclo[4.2.1.0³,⁷]nonan-5-one, (1RS, 2RS)

Sodium hydride (0.27 g; 6.75 mmol of a 60% oil dispersion) was washed by decantation with hexane and then suspended in dry N,N-dimethylacetamide (6 ml, DMAC). A solution of benzyl bromide (1.02 g; 5.96 mmol) in DMAC (5 ml) was added in one portion, and the resultant mixture was cooled in an ice-water bath. A solution of the hydroxylactone from Step B above (1.01 g; 5.49 mmol) in DMAC (5 ml) was then added dropwise at 1°–3° C. over 20 min. After complete addition stirring was continued in the cold for 1 hr and then at room temperature for 21 hr. The reaction solution was poured into water (60 ml) and extracted with methylene chloride (3×75 ml). The combined organic extracts were washed with saturated salt solution (100 ml), dried (MgSO₄), and rotatory evaporated to leave 1.86 g of a pale yellow oil. Purification by flash chromatography (silica gel; 1:1 ether-hexane) provided 0.92 g (61%) of the title ether as a colorless oil.

NMR(CDCl₃, 300 MHz), δ 7.35 (s, 5H), 4.62 (AB quartet, J=12 Hz, 2H), 4.30 (d, J=1 Hz, 1H), 3.50 (s, 1H), 2.52 (d, J=11 Hz, with fine splitting, 1H), 2.15 (d, d, J=13, 11 Hz, 1H), 1.95 (d, d, J=13, 2 Hz, 1H), 1.67 (s, 3H), 1.49 (s, 3H), IR(CH₂Cl₂) 1790 cm⁻¹; MS (SP/CI) 275 (M+1, 100%).

By the general procedures described herein or by modifications obvious to those skilled in the art, the compounds of Tables 1–28 can be prepared. General structures associated with these tables follow:

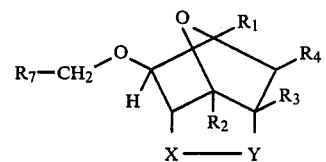

Tables 1–11

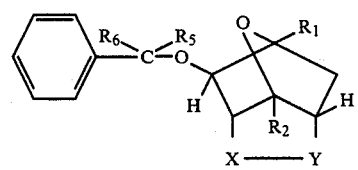

Table 12

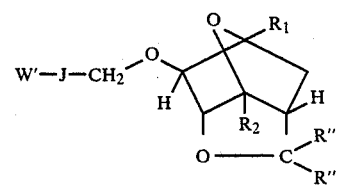

Tables 13–29

As used throughout the Tables, Ph denotes a phenyl group.

TABLE 1

$$X = O, Y = C$$

| $R_1$ | $R_2$ | $R_3$ | $R_4$ | $R_7$ | $R''/R''$ | Properties |
|---|---|---|---|---|---|---|
| H | H | H | H | Ph | H/H | |
| H | $CH_3$ | H | H | Ph | H/H | |
| H | $CH_3$ | $CH_3$ | H | Ph | H/H | |
| H | $CH_3$ | H | $CH_3$ | Ph | H/H | |
| $CH_3$ | H | H | H | Ph | H/H | |
| $CH_3$ | H | $CH_3$ | H | Ph | H/H | |
| $CH_3$ | H | H | $CH_2CH_3$ | Ph | H/H | |
| $CH_3$ | $CH_3$ | H | H | Ph | H/H | pale yellow oil, MS (SP/CI) 261 (M + 1, 12%) |
| $CH_3$ | $CH_3$ | $CH_3$ | H | Ph | H/H | |
| $CH_3$ | $CH_3$ | $CH_2OH$ | H | Ph | H/H | |
| $CH_3$ | $CH_3$ | H | $NO_2$ | Ph | H/H | |
| $CH_3$ | $CH_3$ | $P(O)(OCH_2CH_3)_2$ | H | Ph | H/H | |
| $CH_3$ | $CH_3$ | CN | H | Ph | H/H | |
| $CH_3$ | $CH_3$ | $CO_2CH_2CH_3$ | H | Ph | H/H | |
| $CH_3$ | $CH_3$ | H | H | Ph | $CH_3/CH_3$ | colorless oil, MS (SP/CI) 289 (M + 1, 78%) |
| $CH_3$ | $CH_3$ | $CH_3$ | H | Ph | $CH_3/CH_3$ | |
| $CH_3$ | $CH_3$ | H | $CO_2CH_3$ | Ph | $CH_3/CH_3$ | |
| $CH_3$ | $CH_3$ | H | H | Ph | $CH_2CH_3/CH_2CH_3$ | pale yellow oil, MS (SP/CI) 317 (M + 1, 38%) |
| $CH_3$ | $CH_3$ | H | H | Ph | $CH_3/H$ | |
| $CH_3$ | $CH_3$ | H | H | Ph | $n-CH_2CH_2CH_3/H$ | |
| $CH_3$ | $CH_3$ | $CON(CH_3)_2$ | H | Ph | H/H | |
| $CH_3$ | $CH_3$ | $CONHCH_3$ | H | Ph | H/H | |
| $CH_2CH_3$ | $CH_2CH_3$ | H | H | Ph | H/H | |
| $CH_2CH_3$ | $CH_2CH_3$ | H | H | Ph | $CH_3/CH_3$ | |
| $CH_2CH_3$ | H | H | H | Ph | $CH_2CH_3/CH_2CH_3$ | |
| $CH_2CH_3$ | $CH_3$ | H | H | Ph | H/H | |
| $CH_2CH_3$ | CHO | H | H | Ph | H/H | |
| $CH_2CH_3$ | $CH_2OCH_3$ | H | H | Ph | H/H | |
| $CH_2CH_3$ | Ph | H | H | Ph | H/H | |
| $CH_2CH_3$ | $CH=CH_2$ | H | H | Ph | H/H | |
| $CH_2CH_3$ | $CH_2CN$ | H | H | Ph | H/H | |
| $CH_2CH_3$ | $CH_2OH$ | H | H | Ph | $CH_3/CH_3$ | |
| $CH_3$ | $CH_3$ | H | H | 2-F—Ph | H/H | yellow oil, MS (SP/CI) 279 (M + 1, 34%) |
| $CH_3$ | $CH_3$ | $CH_3$ | H | 2-F—Ph | H/H | |
| $CH_2CH_3$ | $CH_2CH_3$ | H | H | 2-F—Ph | H/H | |
| $CH_2CH_3$ | $CH_2CH_3$ | H | H | 2-F—Ph | $CH_3/CH_3$ | |
| $CH_3$ | $CH_3$ | H | H | 2-F—Ph | $CH_3/CH_3$ | yellow oil, MS (SP/CI) 307 (M + 1, 100%) |
| $CH_3$ | $CH_3$ | H | H | 2-F—Ph | $CH_2CH_3/CH_2CH_3$ | colorless oil, MS (SP/CI) 335 (M + 1, 31%) |
| $CH_3$ | $CH_3$ | H | $CH_3$ | 2-F—Ph | H/H | |
| $CH_3$ | $CH_2SO_2Ph$ | H | H | 2-F—Ph | H/H | |
| $CH_3$ | $CH_3$ | H | H | 2-Cl—Ph | H/H | |
| $CH_3$ | $CH_3$ | H | H | 2-Cl—Ph | $CH_3/CH_3$ | white solid, m.p. 62.5–65° C. |
| $CH_2CH_3$ | $CH_2CH_3$ | H | H | 2-Cl—Ph | H/H | |
| $CH_2CH_3$ | $CH_2CH_3$ | H | H | 2-Cl—Ph | $CH_3/CH_3$ | |
| $CH_2CH_3$ | $CH_2CH_3$ | $CH_3$ | H | 2-Cl—Ph | H/H | |
| $CH_3$ | $CH_3$ | H | H | 2-Cl—Ph | $CH_2CH_3/CH_2CH_3$ | colorless oil, MS (SP/CI) 351 (M + 1, 2%, 1 Cl) |
| $CH_3$ | $CH_2N_3$ | H | H | 2-Cl—Ph | $CH_2CH_2CH_3/H$ | |
| $CH_3$ | $CH_2CO_2CH_3$ | H | H | 2-Cl—Ph | H/H | |
| $CH_3$ | $CH_3$ | H | H | 2-$CH_3$—Ph | H/H | |
| $CH_3$ | $CH_3$ | H | H | 2-$CH_3$—Ph | $CH_3/CH_3$ | colorless oil, MS (SP/CI) 303 (M + 1, 8%) |
| $CH_3$ | $CH_3$ | H | H | 2-$CH_3$—Ph | $H/CH_2CH_3$ | |
| $CH_3$ | $CH_3$ | H | H | 2-$CH_3$—Ph | $CH_2CH_3/CH_2CH_3$ | colorless oil, MS (SP/CI) 331 (M + 1, 4%) |
| $CH_3$ | $CH_2CH_3$ | H | H | 2-$CH_3$—Ph | H/H | |
| $CH_3$ | $CH_2CH_3$ | H | H | 2-$CH_3$—Ph | $CH_3/CH_3$ | |
| $CH_3$ | $CH_2CH_3$ | H | H | 2-$CH_3$—Ph | $CH_2CH_3/CH_2CH_3$ | |
| $CH_2CH_3$ | $CH_2CH_3$ | H | H | 2-$CH_3$—Ph | H/H | |
| $CH_2CH_3$ | $CH_2CH_3$ | H | H | 2-$CH_3$—Ph | $CH_3/CH_3$ | |
| $CH_2CH_3$ | $CH_2CH_3$ | H | H | 2-$CH_3$—Ph | $H/CH_2CH_3$ | |
| $CH_2CH_3$ | $CH_2CH_3$ | H | H | 2-$CH_3$—Ph | $CH_2CH_3/CH_2CH_3$ | |
| $CH_2CH_3$ | $CH_2SO_2CH_3$ | H | H | 2-$CH_3$—Ph | H/H | |

TABLE 1-continued $$X = O, Y = C \overset{R''}{\underset{R''}{\diagdown}}$$

| R₁ | R₂ | R₃ | R₄ | R₇ | R''/R'' | Properties |
|---|---|---|---|---|---|---|
| CH₂CH₃ | CH₂CH₃ | H | H | 2-(CH₃O)—Ph | H/H | |
| CH₂CH₃ | CH₂CH₃ | H | H | 2-(CH₃O)—Ph | CH₃/CH₃ | |
| CH₂CH₃ | CH₂CH₃ | H | H | 2-(CH₃S)—Ph | H/H | |
| CH₂CH₃ | CH₂CH₃ | H | H | 2-(CH₃S)—Ph | CH₂CH₃/CH₂CH₃ | |
| CH₂CH₃ | CH₂CH₃ | H | H | 2-(CH₂SO)—Ph | H/H | |
| CH₂CH₃ | CH₂CH₃ | H | H | 2-(CH₃SO₂)—Ph | CH₃/CH₃ | |
| CH₂CH₃ | CH₂CH₃ | H | H | 3-(NH₂)—Ph | CH₃/CH₃ | |
| CH₂CH₃ | CH₂CH₃ | H | H | 2-(CHO)—Ph | CH₂CH₃/CH₂CH₃ | |
| CH₂CH₃ | CH₂CH₃ | CH₃ | H | 2-CN—Ph | H/H | |
| CH₂CH₃ | CH₂CH₃ | H | H | 1-(OH)—Ph | CH₃/CH₃ | |
| CH₂CH₃ | CH₂CH₃ | H | H | 2-Br—Ph | | |
| CH₂CH₃ | CH₂CH₃ | H | H | 2-(CO₂CH₃)—Ph | H/H | |
| CH₂CH₃ | CH₂CH₃ | H | H | 2-(CHF₂)—Ph | H/H | |
| CH₂CH₃ | CH₂CH₃ | H | H | 2-(C≡CH)—Ph | H/H | |
| CH₂CH₃ | CH₂CH₃ | H | H | 2-(CH=CH₂)—Ph | CH₃/CH₃ | |
| CH₂CH₃ | CH₂CH₃ | H | H | 2-(NHCH₃)—Ph | H/H | |
| CH₂CH₃ | CH₂CH₃ | CH₃ | H | 2-(CONH₂)—Ph | CH₃/CH₃ | |
| CH₂CH₃ | CH₂CH₃ | H | H | 3-(NHCH₃)—Ph | CH₃/CH₃ | |
| CH₃ | CH₃ | H | H | 2,6-(di-Cl)—Ph | CH₃/CH₃ | white solid, m.p. 96-97° C. |
| CH₃ | CH₃ | H | H | 2,6-(di-Cl)—Ph | CH₂CH₃/CH₂CH₃ | |
| CH₃ | CH₂CO₂H | H | H | 2,6-(di-Cl)—Ph | H/H | |
| CH₂CH₃ | CH₂CH₃ | H | H | 2,6-(di-Cl)—Ph | H/H | |
| CH₂CH₃ | CH₂CH₃ | H | H | 2,6-(di-Cl)—Ph | CH₃/CH₃ | |
| CH₂CH₃ | CH₂CH₃ | H | H | 2,6-(di-Cl)—Ph | CH₂CH₃/CH₂CH₃ | |
| CH₃ | CH₃ | CH₃ | H | 2,4-(di-F)—Ph | H/H | |
| CH₃ | CH₃ | H | H | 2,4-(di-F)—Ph | CH₃/CH₃ | |
| CH₃ | CH₃ | H | H | 2,4-(di-F)—Ph | CH₂CH₃/CH₂CH₃ | colorless oil, MS (SP/CI) 353 (M + 1, 100%) |
| CH₃ | CH₂OC(=O)N(CH₃)₂ | H | H | 2,4-(di-F)—Ph | H/H | |
| CH₃ | CH₂OC(=S)N(CH₂CH₃)₂ | H | H | 2,4-(di-F)—Ph | H/H | |
| CH₂CH₃ | CH₂CH₃ | H | H | 2,4-(di-F)—Ph | H/H | |
| CH₂CH₃ | CH₂CH₃ | H | H | 2,4-(di-F)—Ph | CH₃/CH₃ | |
| CH₂CH₃ | CH₂CH₃ | H | H | 2,4-(di-F)—Ph | CH₂CH₃/CH₂CH₃ | |
| CH₃ | CH₃ | H | H | 2,3-(di-F)—Ph | H/H | |
| CH₃ | CH₃ | H | H | 2,3-(di-F)—Ph | CH₃/CH₃ | |
| CH₃ | CH₃ | CH₃ | H | 2,3-(di-F)—Ph | CH₃/CH₃ | |
| CH₃ | CH₃ | H | H | 2,3-(di-F)—Ph | CH₂CH₃/CH₂CH₃ | pale yellow oil, MS (SP/CI) 353 (M + 1, 100%) |
| CH₃ | CH₂P(=O)(OCH₃)₂ | H | H | 2,3-(di-F)—Ph | H/H | |
| CH₂CH₃ | CH₂CH₃ | H | H | 2-Br—Ph | H/H | |
| CH₂CH₃ | CH₂CH₃ | H | H | 2-(CO₂CH₃)—Ph | H/H | |
| CH₂CH₃ | CH₂CH₃ | H | H | 2-(CHF₂)—Ph | H/H | |
| CH₂CH₃ | CH₂CH₃ | H | H | 2-(C≡CH)—Ph | H/H | |
| CH₂CH₃ | CH₂CH₃ | H | H | 2-(CH=CH₂)—Ph | CH₃/CH₃ | |
| CH₂CH₃ | CH₂CH₃ | H | H | 2-(NHCH₃)—Ph | H/H | |
| CH₂CH₃ | CH₂CH₃ | CH | H | 2-(CONH₂)—Ph | CH₃/CH₃ | |
| CH₂CH₃ | CH₂CH₃ | H | H | 3-[N(CH₃)₂]—Ph | CH₃/CH₃ | |
| CH₃ | CH₃ | H | H | 2,6-(di-Cl)—Ph | CH₃/CH₃ | White solid. 96-97° C. |
| CH₃ | CH₃ | H | H | 2,6-(di-Cl)—Ph | CH₂CH₃/CH₂CH₃ | |
| CH₃ | CH₂CO₂H | H | H | 2,6-(di-Cl)—Ph | H/H | |
| CH₂CH₃ | CH₂CH₃ | H | H | 2,6-(di-Cl)—Ph | H/H | |
| CH₂CH₃ | CH₂CH₃ | H | H | 2,6-(di-Cl)—Ph | CH₃/CH₃ | |
| CH₂CH₃ | CH₂CH₃ | H | H | 2,6-(di-Cl)—Ph | CH₂CH₃/CH₂CH₃ | |
| CH₃ | CH₃ | H | H | 2,4-(di-F)—Ph | H/H | |
| CH₃ | CH₃ | H | H | 2,4-(di-F)—Ph | CH₃/CH₃ | |
| CH₃ | CH₃ | H | H | 2,4-(di-F)—Ph | CH₂CH₃/CH₂CH₃ | colorless oil, MS (SP/CI) 353 (M + 1, 100%) |
| CH₃ | CH₂OC(=O)NCH₃ | H | H | 2,4-(di-F)—Ph | H/H | |

TABLE 1-continued $$X = O, Y = C\begin{smallmatrix}R'' \\ \\ R''\end{smallmatrix}$$

| $R_1$ | $R_2$ | $R_3$ | $R_4$ | $R_7$ | $R''/R''$ | Properties |
|---|---|---|---|---|---|---|
| $CH_3$ | $CH_2OC(S)NCH_3CH_3$ | H | H | 2,4-(di-F)—Ph | H/H | |
| $CH_2CH_3$ | $CH_2CH_3$ | H | H | 2,4-(di-F)—Ph | H/H | |
| $CH_2CH_3$ | $CH_2CH_3$ | H | H | 2,4-(di-F)—Ph | $CH_3/CH_3$ | |
| $CH_2CH_3$ | $CH_2CH_3$ | H | H | 2,4-(di-F)—Ph | $CH_2CH_3/CH_2CH_3$ | |
| $CH_3$ | $CH_3$ | H | H | 2,3-(di-F)—Ph | H/H | |
| $CH_3$ | $CH_3$ | H | H | 2,3-(di-F)—Ph | $CH_3/CH_3$ | |
| $CH_3$ | $CH_3$ | $CH_3$ | H | 2,3-(di-F)—Ph | $CH_3/CH_3$ | |
| $CH_3$ | $CH_3$ | H | H | 2,3-(di-F)—Ph | $CH_2CH_3/CH_2CH_3$ | pale yellow oil, MS (SP/CI) 353 (M + 1, 100%) |
| $CH_3$ | $CH_2P(O)(OCH_3)_2$ | H | H | 2,3-(di-F)—Ph | H/H | |
| $CH_2CH_3$ | $CH_2CH_3$ | H | H | 2,3-(di-F)—Ph | H/H | |
| $CH_3$ | $CH_3$ | H | H | 2,6-(di-F)—Ph | H/H | |
| $CH_3$ | $CH_3$ | H | H | 2,6-(di-F)—Ph | $CH_3/CH_3$ | |
| $CH_3$ | $CH_3$ | H | H | 2,6-(di-F)—Ph | $CH_2CH_3/CH_2CH_3$ | colorless oil, MS (SP/CI) 353 (M + 1, 59%) |
| $CH_3$ | $CH_2OC(O)NHCH_3$ | H | H | 2,6-(di-F)—Ph | H/H | |
| $CH_2CH_3$ | $CH_2CH_3$ | H | $CH_3$ | 2,6-(di-F)—Ph | H/H | |
| $CH_2CH_3$ | $CH_2CH_3$ | H | H | 2,6-(di-F)—Ph | $CH_3/CH_3$ | |
| $CH_3$ | H | H | H | 2-Cl—6-F—Ph | H/H | |
| $CH_3$ | $CH_3$ | H | H | 2-Cl—6-F—Ph | H/H | colorless oil, MS (SP/CI) 313 (M + 1, 19%, 1 Cl) |
| $CH_3$ | $CH_3$ | H | H | 2-Cl—6-F—Ph | $CH_3/H$ | |
| $CH_3$ | $CH_3$ | H | H | 2-Cl—6-F—Ph | $CH_3/CH_3$ | |
| $CH_3$ | $CH_3$ | H | H | 2-Cl—6-F—Ph | $CH_2CH_3/CH_2CH_3$ | colorless oil, MS (SP/CI) 371 (M + 1, 37%, 1 Cl) |
| $CH_3$ | $CH_2C\equiv CH$ | H | H | 2-Cl—6-F—Ph | H/H | |
| $CH_3$ | $CH_2Ph$ | H | H | 2-Cl—6-F—Ph | H/H | |
| $CH_3$ | $CH_2OP(O)(OCH_2CH_3)_2$ | H | H | 2-Cl—6-F—Ph | H/H | |

TABLE 2

$X = O, Y = C(O)$

| $R_1$ | $R_2$ | $R_3$ | $R_4$ | $R_7$ | Properties |
|---|---|---|---|---|---|
| $CH_3$ | H | H | H | Ph | |
| $CH_3$ | $CH_3$ | H | H | Ph | colorless oil, MS (SP/CI) 275 (M + 1, 100%, IR 1790 cm$^{-1}$) |
| $CH_3$ | $CH_3$ | $CH_2OCH_3$ | H | Ph | |
| $CH_3$ | $CH_3$ | $CH_2SCH_3$ | H | Ph | |
| $CH_2CH_3$ | $CH_2CH_3$ | H | H | Ph | |
| $CH_2CH_3$ | $CH_2CH_3$ | H | $CH_3$ | Ph | |
| $CH_2CH_3$ | $CH_2CH_3$ | $CH_2CN$ | H | Ph | |
| $CH_3$ | $CH_3$ | H | H | 2-F—Ph | colorless oil, MS (SP/CI) 293 (M + 1, 100%, IR 1790 cm$^{-1}$) |
| $CH_3$ | $CH_3$ | Cl | H | 2-F—Ph | |
| $CH_2CH_3$ | $CH_2CH_3$ | Cl | H | 2-F—Ph | |
| $CH_2CH_3$ | $CH_2CH_3$ | $CH_3$ | H | 2-F—Ph | |
| $CH_2CH_3$ | $CH_2CH_3$ | H | H | 1-F—Ph | |
| $CH_3$ | H | H | H | 2-$CH_3$—Ph | |
| $CH_3$ | $CH_3$ | H | H | 2-$CH_3$—Ph | colorless oil, MS (SP/CI) 289 (M + 1, 80%, IR 1790 cm$^{-1}$) |
| $CH_3$ | $CH_3$ | $C(O)CH_3$ | H | 2-$CH_3$—Ph | |
| $CH_2CH_3$ | H | $C(O)CH_2CH_3$ | H | 2-$CH_3$—Ph | |
| $CH_2CH_3$ | $CH_2CH_3$ | H | H | 2-$CH_3$—Ph | |
| $CH_3$ | $CH_3$ | H | H | 2-Cl—Ph | |
| $CH_3$ | $CH_3$ | H | $OCH_3$ | 2-Cl—Ph | |
| $CH_3$ | $CH_3$ | H | $CO_2CH_3$ | 2-Cl—Ph | |

TABLE 2-continued

X = O, Y = C(O)

| R₁ | R₂ | R₃ | R₄ | R₇ | Properties |
|---|---|---|---|---|---|
| CH₃ | CH₃ | H | C(O)NHCH₃ | 2-Cl—Ph | |
| CH₃ | CH₃ | H | C(O)N(CH₃)₂ | 2-Cl—Ph | |
| CH₂CH₃ | CH₂CH₃ | H | H | 2-Cl—Ph | |
| CH₃ | CH₃ | H | H | 2-Cl—6-F—Ph | white solid, m.p. 128.5–129.5 |
| CH₃ | CH₃ | H | CN | 2-Cl—6-F—Ph | |
| CH₂CH₃ | CH₂CH₃ | Cl | H | 2-Cl—6-F—Ph | |
| CH₂CH₃ | CH₂CH₃ | CH₃ | H | 2-Cl—6-F—Ph | |
| CH₂CH₃ | CH₂CH₃ | H | CN | 2-Cl—6-F—Ph | |
| CH₃ | CH₃ | H | H | 2,6-di-Cl—Ph | |
| CH₂CH₃ | CH₂CH₃ | H | H | 2,6-di-Cl—Ph | |

TABLE 3

X = NR′, Y = C(O)

| R₁ | R₂ | R₃ | R₄ | R₇ | R′ | Properties |
|---|---|---|---|---|---|---|
| CH₃ | CH₃ | H | H | Ph | H | |
| CH₃ | CH₃ | H | H | Ph | CH₃ | |
| CH₃ | CH₃ | H | H | Ph | Ph | |
| CH₃ | CH₃ | Cl | H | Ph | H | |
| CH₃ | CH₃ | Cl | H | Ph | CH₃ | |
| CH₂CH₃ | CH₂CH₃ | H | H | Ph | H | |
| CH₃ | CH₃ | H | H | Ph | CH₃ | |
| CH₂CH₃ | CH₂CH₃ | H | H | Ph | Ph | |
| CH₂CH₃ | CH₂CH₃ | Cl | H | Ph | H | |
| CH₂CH₃ | CH₂CH₃ | Cl | H | Ph | CH₂CH₃ | |
| CH₃ | CH₃ | H | H | 2-F—Ph | H | |
| CH₃ | CH₃ | H | H | 2-F—Ph | CH₃ | |
| CH₃ | CH₃ | Cl | H | 2-F—Ph | H | |
| CH₃ | CH₃ | CH₂OCH₃ | H | 2-F—Ph | H | |
| CH₂CH₃ | CH₂CH₃ | H | H | 2-F—Ph | H | |
| CH₂CH₃ | CH₂CH₃ | H | H | 2-F—Ph | H | |
| CH₂CH₃ | CH₂CH₃ | H | H | 2-F—Ph | CH₃ | |
| CH₂CH₃ | CH₂CH₃ | H | H | 2-F—Ph | Ph | |
| CH₃ | CH₃ | H | H | 2-Cl—6-F—Ph | H | |
| CH₃ | CH₃ | H | CH₃ | 2-Cl—6-F—Ph | CH₂CH₃ | |
| CH₂CH₃ | CH₂CH₃ | H | H | 2-Cl—6-F—Ph | H | |
| CH₂CH₃ | CH₂CH₃ | H | H | 2-Cl—6-F—Ph | CH₃ | |
| CH₃ | CH₃ | H | H | 2-CH₃—Ph | H | |
| CH₃ | CH₃ | H | H | 2-CH₃—Ph | CH₃ | |

TABLE 4

X = S, Y = CH₂

| R₁ | R₂ | R₃ | R₄ | R₇ | Properties |
|---|---|---|---|---|---|
| CH₃ | CH₃ | H | H | Ph | |
| CH₂CH₃ | CH₂CH₃ | H | H | Ph | |
| CH₃ | CH₃ | H | H | 2-Cl—Ph | |
| CH₃ | CH₃ | CH₃ | H | 2-Cl—Ph | |
| CH₂CH₃ | CH₂CH₃ | H | H | 2-Cl—Ph | |
| CH₃ | CH₃ | H | H | 2-F—Ph | |
| CH₂CH₃ | CH₂CH₃ | H | H | 2-F—Ph | |
| CH₃ | CH₃ | H | H | 2-Cl—6-F—Ph | |
| CH₃ | CH₃ | CH₂OCH₃ | H | 2-Cl—6-F—Ph | |
| CH₂CH₃ | CH₂CH₃ | H | H | 2-Cl—6-F—Ph | |
| CH₂CH₃ | CH₂CH₃ | H | H | 2-CH₃—Ph | |

TABLE 5

$X = C\begin{smallmatrix}R'\\R'\end{smallmatrix}$, Y = C(O)

| R₁ | R₂ | R₃ | R₄ | R₇ | R′/R′ | Properties |
|---|---|---|---|---|---|---|
| CH₃ | CH₃ | H | H | Ph | H/H | |
| CH₃ | CH₃ | H | H | Ph | H/CH₃ | |
| CH₃ | CH₃ | H | H | Ph | H/Ph | |
| CH₃ | CH₃ | H | H | Ph | CH₃/CH₃ | |
| CH₂CH₃ | CH₂CH₃ | H | H | Ph | H/H | |
| CH₂CH₃ | CH₂CH₃ | H | H | Ph | CH₃/CH₃ | |
| CH₃ | CH₃ | H | H | 2,3-di-F—Ph | H/H | |

TABLE 5-continued

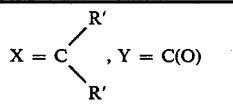

$X = C\begin{smallmatrix}R'\\R'\end{smallmatrix}$, Y = C(O)

| R₁ | R₂ | R₃ | R₄ | R₇ | R′/R′ | Properties |
|---|---|---|---|---|---|---|
| CH₃ | CH₃ | H | H | 2,3-di-F—Ph | CH₃/CH₃ | |
| CH₂CH₃ | CH₂CH₃ | H | H | 2,3-di-F—Ph | H/H | |
| CH₃ | CH₃ | H | H | 2,6-di-F—Ph | H/H | |
| CH₂CH₃ | CH₂CH₃ | H | H | 2,6-di-F—Ph | H/CH₃ | |
| CH₂CH₃ | CH₃ | H | H | 2-Br—Ph | H/H | |
| CH₃ | CH₂CH₃ | H | H | 2-Br—Ph | H/H | |

TABLE 6

$X = C\begin{smallmatrix}R'\\R'\end{smallmatrix}$, $Y = C\begin{smallmatrix}R''\\R''\end{smallmatrix}$

| R₁ | R₂ | R₃ | R₄ | R₇ | R′/R′ | R″/R″ | Properties |
|---|---|---|---|---|---|---|---|
| CH₃ | CH₃ | H | H | Ph | H/H | H/H | |
| CH₃ | CH₃ | H | H | Ph | H/CH₃ | H/CH₃ | |
| CH₃ | CH₃ | H | H | Ph | H/Ph | H/H | |
| CH₃ | CH₃ | H | H | Ph | H/Ph | H/CH₃ | |
| CH₃ | CH₃ | H | H | 2-F—Ph | H/H | H/H | |
| CH₂CH₃ | CH₂CH₃ | H | H | Ph | H/H | H/H | |

TABLE 6-continued

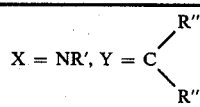

| R₁ | R₂ | R₃ | R₄ | R₇ | R'/R' | R"/R" | Properties |
|---|---|---|---|---|---|---|---|
| CH₂CH₃ | CH₂CH₃ | H | H | 2-CH₃Ph | H/H | H/H | |

TABLE 7

$$X = NR', Y = C\begin{matrix}R''\\R''\end{matrix}$$

| R₁ | R₂ | R₃ | R₄ | R₇ | R' | R"/R" | Properties |
|---|---|---|---|---|---|---|---|
| CH₃ | CH₃ | H | H | Ph | H | H/H | |
| CH₃ | CH₃ | H | H | Ph | H | H/CH₃ | |
| CH₃ | CH₃ | H | H | Ph | H | CH₃/CH₃ | |
| CH₂CH₃ | CH₂CH₃ | H | H | Ph | CH₃ | H/H | |
| CH₃ | CH₃ | H | H | 2-CH₃—Ph | H | H/H | |
| CH₃ | CH₃ | H | CH₃ | 2-CH₃—Ph | CH₃ | H/H | |
| CH₂CH₃ | CH₂CH₃ | H | H | 2-CH₃—Ph | H | H/H | |
| CH₃ | CH₃ | H | H | 2-Cl—6-F—Ph | CH₃ | H/H | |
| CH₃ | CH₃ | H | H | 2-Cl—6-F—Ph | H | H/H | |
| CH₃ | CH₂OCH₃ | H | H | 2-Cl—6-F—Ph | CH₂CH₃ | H/H | |
| CH₂CH₃ | CH₂CH₃ | H | H | 2-Cl—6-F—Ph | Ph | H/H | |

TABLE 8

X = CH₂, Y = S(O)ₙ

| R₁ | R₂ | R₃ | R₄ | R₇ | n | Properties |
|---|---|---|---|---|---|---|
| CH₃ | CH₃ | H | H | Ph | 1 | |
| CH₃ | CH₃ | H | H | Ph | 2 | |
| CH₂CH₃ | CH₂CH₃ | H | H | Ph | 1 | |
| CH₂CH₃ | CH₂CH₃ | H | H | Ph | 2 | |
| CH₃ | CH₃ | H | H | 2-F—Ph | 1 | |
| CH₃ | CH₃ | H | H | 2-F—Ph | 2 | |
| CH₃ | CH₂CH₃ | H | H | 2-F—Ph | 1 | |
| CH₃ | CH₂CH₃ | H | H | 2-F—Ph | 2 | |
| CH₂CH₃ | CH₃ | H | H | 2-F—Ph | 1 | |
| CH₂CH₃ | CH₃ | H | H | 2-F—Ph | 2 | |
| CH₂CH₃ | CH₂CH₃ | H | H | 2-F—Ph | 1 | |
| CH₂CH₃ | CH₂CH₃ | H | H | 2-F—Ph | 2 | |
| CH₃ | CH₃ | H | H | 2-Cl—Ph | 1 | |
| CH₃ | CH₃ | H | H | 2-Cl—Ph | 2 | |
| CH₂CH₃ | CH₂CH₃ | H | H | 2-Cl—Ph | 1 | |
| CH₂CH₃ | CH₂CH₃ | H | H | 2-Cl—Ph | 2 | |
| CH₃ | CH₃ | H | H | 2,6-di-Cl—Ph | 1 | |
| CH₃ | CH₃ | H | H | 2,6-di-Cl—Ph | 2 | |
| CH₂CH₃ | CH₂CH₃ | H | H | 2,6-di-Cl—Ph | 1 | |
| CH₂CH₃ | CH₂CH₃ | H | H | 2,6-di-Cl—Ph | 2 | |

TABLE 9

X = O, Y = S(O)₂

| R₁ | R₂ | R₃ | R₄ | R₇ | Properties |
|---|---|---|---|---|---|
| CH₃ | CH₃ | H | H | Ph | |
| CH₃ | CH₂CH₃ | H | H | Ph | |
| CH₂CH₃ | CH₃ | H | H | Ph | |
| CH₂CH₃ | CH₂CH₃ | H | H | Ph | |
| CH₃ | CH₃ | H | H | 2,6-di-F—Ph | |
| CH₂CH₃ | CH₂CH₃ | H | H | 2,6-di-F—Ph | |
| CH₃ | CH₃ | H | H | 2-Cl—6-F—Ph | |
| CH₂CH₃ | CH₂CH₃ | H | H | 2-Cl—6-F—Ph | |
| CH₃ | CH₃ | H | H | 2,6-di-Cl—Ph | |
| CH₂CH₃ | CH₂CH₃ | H | H | 2,6-di-Cl—Ph | |
| CH₃ | CH₃ | H | H | 2-Br—Ph | |
| CH₂CH₃ | CH₂CH₃ | H | H | 2-Br—Ph | |

TABLE 10

X = NR', Y = S(O)₂

| R₁ | R₂ | R₃ | R₄ | R₇ | R' | Properties |
|---|---|---|---|---|---|---|
| CH₃ | CH₃ | H | H | Ph | H | |
| CH₃ | CH₃ | H | H | Ph | CH₃ | |
| CH₃ | CH₃ | H | H | Ph | Ph | |
| CH₂CH₃ | CH₂CH₃ | H | H | Ph | H | |
| CH₂CH₃ | CH₂CH₃ | H | H | Ph | H | |
| CH₂CH₃ | CH₂CH₃ | H | H | Ph | CH₃ | |
| CH₂CH₃ | CH₂CH₃ | H | H | Ph | Ph | |
| CH₃ | CH₃ | H | H | 2-F—Ph | H | |
| CH₃ | CH₃ | H | H | 2-F—Ph | CH₂CH₃ | |
| CH₃ | CH₃ | H | H | 2-F—Ph | Ph | |
| CH₂CH₃ | CH₂CH₃ | H | H | 2-F—Ph | H | |
| CH₂CH₃ | CH₂CH₃ | H | H | 2-F—Ph | Ph | |
| CH₂CH₃ | CH₂CH₃ | H | H | 2-F—Ph | CH₃ | |
| CH₃ | CH₃ | H | H | 2-CH₃—Ph | H | |
| CH₃ | CH₃ | H | H | 2-CH₃—Ph | CH₃ | |
| CH₃ | CH₃ | H | H | 2-CH₃—Ph | n-CH₂CH₂CH₃ | |
| CH₂CH₃ | CH₂CH₃ | H | H | 2-CH₃—Ph | H | |
| CH₂CH₃ | CH₂CH₃ | H | H | 2-CH₃—Ph | CH₃ | |
| CH₂CH₃ | CH₂CH₃ | H | H | 2-CH₃—Ph | CH₂CH₃ | |

TABLE 11

X = O, Y = P(O)(ORa)

| R₁ | R₂ | R₃ | R₄ | R₇ | Ra | Properties |
|---|---|---|---|---|---|---|
| CH₃ | CH₃ | H | H | Ph | CH₃ | |
| CH₃ | CH₃ | H | H | Ph | CH₂CH₃ | |
| CH₂CH₃ | CH₂CH₃ | H | H | Ph | CH₃ | |
| CH₂CH₃ | CH₂CH₃ | H | H | Ph | CH₂CH₃ | |
| CH₃ | CH₃ | H | H | 2,3-diF—Ph | CH₃ | |
| CH₃ | CH₃ | H | H | 2,3-di-F—Ph | CH₂CH₃ | |
| CH₂CH₃ | CH₂CH₃ | H | H | 2,3-di-F—Ph | CH₃ | |
| CH₂CH₃ | CH₂CH₃ | H | H | 2,3-diF—Ph | CH₂CH₃ | |
| CH₃ | CH₃ | H | H | 2,6-di-F—Ph | CH₃ | |
| CH₃ | CH₃ | H | H | 2,6-di-F—Ph | CH₂CH₃ | |
| CH₃ | CH₂CH₃ | H | H | 2,6-di-F—Ph | CH₃ | |
| CH₃ | CH₂CH₃ | H | H | 2,6-di-F—Ph | CH₂CH₃ | |
| CH₂CH₃ | CH₃ | H | H | 2,6-di-F—Ph | CH₃ | |
| CH₂CH₃ | CH₃ | H | H | 2,6-di-F—Ph | CH₂CH₃ | |
| CH₂CH₃ | CH₂CH₃ | H | H | 2,6-di-F—Ph | CH₃ | |
| CH₂CH₃ | CH₂CH₃ | H | H | 2-Cl—6-F—Ph | CH₃ | |

TABLE 12

$$X = O, Y = C\begin{matrix}R''\\R''\end{matrix}$$

| R₁ | R₂ | R₅ | R₆ | R"/R" | Properties |
|---|---|---|---|---|---|
| CH₃ | CH₃ | H | CH₃ | H/H | |
| CH₃ | CH₃ | H | CH₃ | CH₂CH₃/CH₂CH₃ | |
| CH₂CH₃ | CH₂CH₃ | H | CH₃ | H/H | |

TABLE 12-continued

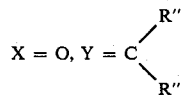

X = O, Y = C(R″)(R″)

| R₁ | R₂ | R₅ | R₆ | R″/R″ | Properties |
|---|---|---|---|---|---|
| CH₂CH₃ | CH₂CH₃ | H | CH₃ | CH₃/CH₃ | |
| CH₂CH₃ | CH₂CH₃ | H | CH₃ | CH₂CH₃/CH₂CH₃ | |
| CH₃ | CH₃ | H | F | H/H | |
| CH₃ | CH₃ | H | F | CH₃/CH₃ | |
| CH₃ | CH₃ | H | F | CH₂CH₃/CH₂CH₃ | |
| CH₂CH₃ | CH₂CH₃ | H | F | H/H | |
| CH₂CH₃ | CH₂CH₃ | H | F | CH₃/CH₃ | |
| CH₂CH₃ | CH₂CH₃ | H | F | CH₂CH₃/CH₂CH₃ | |
| CH₃ | CH₃ | F | F | H/H | |
| CH₃ | CH₃ | F | F | CH₃/CH₃ | |
| CH₃ | CH₃ | F | F | CH₂CH₃/CH₂CH₃ | |
| CH₂CH₃ | CH₂CH₃ | F | F | CH₃/CH₃ | |
| CH₂CH₃ | CH₂CH₃ | F | F | CH₂CH₃/CH₂CH₃ | |
| CH₂CH₃ | CH₂CH₃ | F | F | H/H | |

TABLE 13

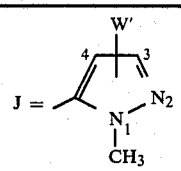

| R₁ | R₂ | R″ | W′ | Properties |
|---|---|---|---|---|
| CH₃ | CH₃ | H | — | |
| CH₃ | CH₃ | CH₃ | — | |
| CH₃ | CH₃ | CH₂CH₃ | — | |
| CH₂CH₃ | CH₂CH₃ | H | — | |
| CH₂CH₃ | CH₂CH₃ | CH₃ | — | |
| CH₂CH₃ | CH₂CH₃ | CH₂CH₃ | — | |
| CH₂CH₃ | CH₂CH₃ | H | 4-CH₃ | |
| CH₂CH₃ | CH₂CH₃ | CH₃ | 4-CH₃ | |
| CH₃ | CH₃ | CH₂CH₃ | 4-CH₃ | |
| CH₃ | CH₃ | H | 4-CH₃ | |
| CH₃ | CH₃ | H | 4-Cl | |
| CH₃ | CH₃ | CH₃ | 4-Cl | |
| CH₃ | CH₃ | CH₂CH₃ | 4-Cl | |
| CH₃ | CH₃ | CH₂CH₃ | 4-Cl | |
| CH₂CH₃ | CH₂CH₃ | CH₂CH₃ | 4-Cl | |
| CH₂CH₃ | CH₂CH₃ | H | 4-Cl | |
| CH₂CH₃ | CH₂CH₃ | CH₃ | 4-Cl | |

TABLE 14

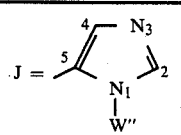

| R₁ | R₂ | R″ | W″ | Properties |
|---|---|---|---|---|
| CH₃ | CH₃ | H | CH₃ | |
| CH₃ | CH₃ | CH₃ | CH₃ | |
| CH₃ | CH₃ | CH₂CH₃ | CH₃ | |
| CH₂CH₃ | CH₂CH₃ | CH₂CH₃ | CH₃ | |
| CH₂CH₃ | CH₂CH₃ | H | CH₃ | |
| CH₂CH₃ | CH₂CH₃ | CH₃ | CH₃ | |
| CH₂CH₃ | CH₂CH₃ | CH₃ | CH₃ | |
| CH₂CH₃ | CH₂CH₃ | CH₃ | CH₂CH₃ | |
| CH₂CH₃ | CH₂CH₃ | H | CH₂CH₃ | |
| CH₃ | CH₃ | H | CH₂CH₃ | |
| CH₃ | CH₃ | CH₃ | CH₂CH₃ | |
| CH₃ | CH₃ | CH₂CH₃ | CH₂CH₃ | |

TABLE 15

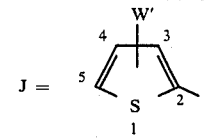

| R₁ | R₂ | R″ | W′ | Properteis |
|---|---|---|---|---|
| CH₃ | CH₃ | H | 3-Cl | |
| CH₃ | CH₃ | CH₃ | 3-Cl | |
| CH₃ | CH₃ | CH₂CH₃ | 3-Cl | |
| CH₂CH₃ | CH₂CH₃ | H | 3-Cl | |
| CH₂CH₃ | CH₂CH₃ | CH₃ | 3-Cl | |
| CH₂CH₃ | CH₂CH₃ | CH₂CH₃ | 3-Cl | |
| CH₃ | CH₃ | H | 3-CH₃ | |
| CH₃ | CH₃ | CH₃ | 3-CH₃ | |
| CH₂CH₃ | CH₃ | H | 3-CH₃ | |
| CH₂CH₃ | CH₃ | CH₃ | 3-CH₃ | |
| CH₂CH₃ | CH₂CH₃ | CH₃ | 3-CH₃ | |
| CH₂CH₃ | CH₂CH₃ | CH₂CH₃ | 3-CH₃ | |
| CH₂CH₃ | CH₃ | H | 3-CH₃ | |
| CH₃ | CH₃ | H | 3-Br | |
| CH₂CH₃ | CH₂CH₃ | H | 3-Br | |
| CH₂CH₃ | CH₂CH₃ | H | H | |
| CH₂CH₃ | CH₂CH₃ | CH₃ | H | |
| CH₂CH₃ | CH₂CH₃ | CH₂CH₃ | H | |
| CH₃ | CH₃ | H | H | |
| CH₃ | CH₃ | CH₃ | H | |
| CH₃ | CH₃ | H | 3,4-di-Cl | |
| CH₂CH₃ | CH₂CH₃ | CH₃ | 3,4-di-Cl | |

TABLE 16

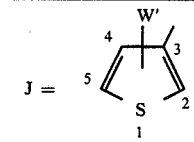

| R₁ | R₂ | R″ | W′ | Properties |
|---|---|---|---|---|
| CH₃ | CH₃ | H | 2-CH₃ | |
| CH₃ | CH₃ | CH₃ | 2-CH₃ | |
| CH₃ | CH₃ | CH₂CH₃ | 2-CH₃ | |
| CH₂CH₃ | CH₂CH₃ | H | 2-CH₃ | |
| CH₂CH₃ | CH₂CH₃ | CH₃ | 2-CH₃ | |
| CH₂CH₃ | CH₂CH₃ | CH₂CH₃ | 2-CH₃ | |
| CH₂CH₃ | CH₂CH₃ | H | 2-Br | |
| CH₂CH₃ | CH₂CH₃ | CH₃ | 2-Br | |
| CH₃ | CH₃ | CH₃ | 2-Br | |
| CH₃ | CH₃ | H | 2-Br | |
| CH₃ | CH₃ | H | 4-CH₃ | |
| CH₃ | CH₃ | CH₂CH₃ | 4-CH₃ | |
| CH₂CH₃ | CH₂CH₃ | CH₃ | 4-CH₃ | |
| CH₂CH₃ | CH₂CH₃ | H | 4-CH₃ | |

TABLE 17

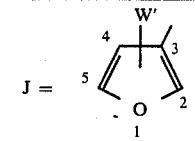

| R₁ | R₂ | R″ | W′ | Properties |
|---|---|---|---|---|
| CH₃ | CH₃ | H | H | |
| CH₃ | CH₃ | CH₃ | H | |
| CH₃ | CH₃ | CH₂CH₃ | H | |
| CH₂CH₃ | CH₂CH₃ | CH₂CH₃ | H | |
| CH₂CH₃ | CH₂CH₃ | H | H | |
| CH₂CH₃ | CH₂CH₃ | CH₃ | H | |
| CH₂CH₃ | CH₂CH₃ | H | 2-CH₃ | |
| CH₂CH₃ | CH₂CH₃ | CH₃ | 2-CH₃ | |
| CH₂CH₃ | CH₂CH₃ | CH₂CH₃ | 2-CH₃ | |
| CH₃ | CH₃ | H | 2-CH₃ | |
| CH₃ | CH₃ | CH₂CH₃ | 2-CH₃ | |

TABLE 17-continued

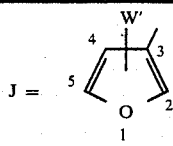

| R₁ | R₂ | R" | W' | Properties |
|---|---|---|---|---|
| CH₃ | CH₃ | CH₃ | 2-CH₃ | |

TABLE 18

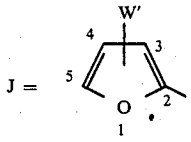

| R₁ | R₂ | R" | W' | Properties |
|---|---|---|---|---|
| CH₃ | CH₃ | H | 3-CH₃ | |
| CH₃ | CH₃ | CH₃ | 3-CH₃ | |
| CH₃ | CH₃ | CH₂CH₃ | 3-CH₃ | |
| CH₂CH₃ | CH₂CH₃ | H | 3-CH₃ | |
| CH₂CH₃ | CH₂CH₃ | CH₃ | 3-CH₃ | |
| CH₂CH₃ | CH₂CH₃ | CH₂CH₃ | 3-CH₃ | |
| CH₂CH₃ | CH₂CH₃ | H | 3-Br | |
| CH₂CH₃ | CH₂CH₃ | CH₃ | 3-Br | |
| CH₃ | CH₃ | H | 3-Br | |
| CH₃ | CH₃ | CH₂CH₃ | 3-Br | |
| CH₃ | CH₃ | CH₂CH₃ | H | |
| CH₃ | CH₃ | CH₃ | H | |
| CH₃ | CH₃ | H | H | |
| CH₂CH₃ | CH₂CH₃ | CH₃ | H | |
| CH₂CH₃ | CH₂CH₃ | H | H | |
| CH₂CH₃ | CH₂CH₃ | CH₂CH₃ | H | |

TABLE 19

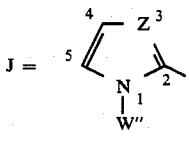

| R₁ | R₂ | R" | W" | Z | Properties |
|---|---|---|---|---|---|
| CH₃ | CH₃ | H | CH₃ | CH | |
| CH₃ | CH₃ | CH₃ | CH₃ | CH | |
| CH₂CH₃ | CH₂CH₃ | H | CH₃ | CH | |
| CH₂CH₃ | CH₂CH₃ | CH₃ | CH₃ | CH | |
| CH₂CH₃ | CH₂CH₃ | H | CH₃ | N | |
| CH₂CH₃ | CH₂CH₃ | CH₂CH₃ | CH₃ | N | |
| CH₃ | CH₃ | H | CH₃ | N | |
| CH₃ | CH₃ | CH₃ | CH₃ | N | |
| CH₃ | CH₃ | H | CH₂CH₃ | N | |
| CH₃ | CH₃ | H | CH₂CH₃ | CH | |
| CH₂CH₃ | CH₂CH₃ | CH₃ | CH₂CH₃ | CH | |

TABLE 20

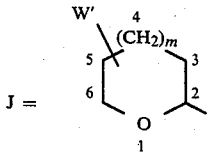

| R₁ | R₂ | R" | W' | m | Properties |
|---|---|---|---|---|---|
| CH₃ | CH₃ | H | H | 0 | |
| CH₃ | CH₃ | H | H | 1 | |
| CH₃ | CH₃ | CH₃ | H | 0 | |
| CH₃ | CH₃ | CH₃ | H | 1 | |
| CH₃ | CH₃ | CH₂CH₃ | H | 0 | |
| CH₃ | CH₃ | CH₂CH₃ | H | 1 | |

TABLE 20-continued

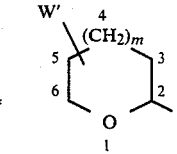

| R₁ | R₂ | R" | W' | m | Properties |
|---|---|---|---|---|---|
| CH₃ | CH₃ | H | 6-CH₃ | 1 | |
| CH₃ | CH₃ | CH₃ | 6-CH₃ | 1 | |
| CH₂CH₃ | CH₂CH₃ | H | H | 0 | |
| CH₂CH₃ | CH₂CH₃ | H | H | 1 | |
| CH₂CH₃ | CH₂CH₃ | CH₃ | H | 0 | |
| CH₂CH₃ | CH₂CH₃ | CH₃ | H | 1 | |
| CH₂CH₃ | CH₂CH₃ | CH₂CH₃ | H | 0 | |
| CH₂CH₃ | CH₂CH₃ | CH₂CH₃ | H | 1 | |
| CH₃ | CH₃ | H | 4-CH₃ | 1 | |
| CH₃ | CH₃ | CH₂CH₃ | 4-CH₃ | 1 | |
| CH₂CH₃ | CH₂CH₃ | H | 4-CH₃ | 1 | |
| CH₂CH₃ | CH₂CH₃ | CH₃ | 4-CH₃ | 1 | |
| CH₂CH₃ | CH₂CH₃ | H | 5-CH₃ | 1 | |
| CH₂CH₃ | CH₂CH₃ | CH₃ | 5-CH₃ | 1 | |
| CH₃ | CH₃ | CH₃ | 5-CH₃ | 1 | |
| CH₃ | CH₃ | H | 5-CH₃ | 1 | |
| CH₂CH₃ | CH₂CH₃ | CH₃ | 5-OCH₃ | 1 | |

TABLE 21

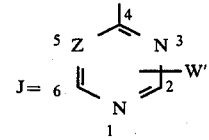

| R₁ | R₂ | R" | W' | Z | Properties |
|---|---|---|---|---|---|
| CH₃ | CH₃ | H | 5-Cl | CH | |
| CH₃ | CH₃ | CH₃ | 5-Cl | CH | |
| CH₂CH₃ | CH₂CH₃ | H | 5-Cl | CH | |
| CH₂CH₃ | CH₂CH₃ | CH₂CH₃ | 5-Cl | CH | |
| CH₃ | CH₃ | H | 2-SCH₃, 5-Cl | CH | |
| CH₂CH₃ | CH₂CH₃ | H | 2-SCH₃, 5-Cl | CH | |
| CH₂CH₃ | CH₂CH₃ | CH₃ | 2-OCH₃, 5-Cl | CH | |
| CH₃ | CH₃ | H | 2-OCH₃, 5-Cl | CH | |
| CH₃ | CH₃ | H | 2-OCH₃ | CH | |
| CH₂CH₃ | CH₂CH₃ | H | 2-OCH₃ | CH | |
| CH₃ | CH₃ | CH₃ | 2,6-(OCH₃)₂ | N | |
| CH₂CH₃ | CH₂CH₃ | CH₃ | 2,6-(OCH₃)₂ | N | |

TABLE 22

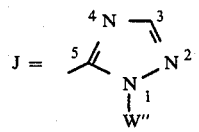

| R₁ | R₂ | R" | W" | Properties |
|---|---|---|---|---|
| CH₃ | CH₃ | H | CH₃ | |
| CH₃ | CH₃ | CH₃ | CH₃ | |
| CH₃ | CH₃ | CH₂CH₃ | CH₃ | |
| CH₂CH₃ | CH₂CH₃ | CH₂CH₃ | CH₃ | |
| CH₂CH₃ | CH₂CH₃ | H | CH₃ | |
| CH₂CH₃ | CH₂CH₃ | CH₃ | CH₃ | |
| CH₃ | CH₃ | H | CH₂CH₃ | |
| CH₂CH₃ | CH₂CH₃ | H | CH₂CH₃ | |
| CH₂CH₃ | CH₂CH₃ | CH₃ | CH₂CH₃ | |

TABLE 23

J = 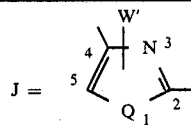

| R₁ | R₂ | R'' | W' | Q | Properties |
|---|---|---|---|---|---|
| CH₃ | CH₃ | H | H | O | |
| CH₃ | CH₃ | H | H | S | |
| CH₃ | CH₃ | CH₃ | H | O | |
| CH₃ | CH₃ | CH₃ | H | S | |
| CH₂CH₃ | CH₂CH₃ | CH₃ | H | S | |
| CH₂CH₃ | CH₂CH₃ | CH₃ | H | O | |
| CH₂CH₃ | CH₂CH₃ | H | H | O | |
| CH₂CH₃ | CH₂CH₃ | H | H | S | |
| CH₂CH₃ | CH₂CH₃ | H | 5-CH₃ | O | |
| CH₂CH₃ | CH₂CH₃ | CH₃ | 5-CH₃ | O | |
| CH₂CH₃ | CH₂CH₃ | H | 5-CH₃ | S | |
| CH₂CH₃ | CH₂CH₃ | CH₃ | 5-CH₃ | S | |
| CH₃ | CH₃ | H | 5-CH₃ | S | |
| CH₃ | CH₃ | H | 5-CH₃ | O | |
| CH₃ | CH₃ | CH₃ | 5-CH₃ | S | |
| CH₃ | CH₃ | CH₃ | 5-CH₃ | O | |
| CH₃ | CH₃ | H | 5-Cl | S | |
| CH₃ | CH₃ | H | 5-Cl | O | |
| CH₃ | CH₃ | CH₃ | 5-Cl | O | |
| CH₃ | CH₃ | CH₃ | 5-Cl | S | |
| CH₂CH₃ | CH₂CH₃ | H | 5-Cl | O | |
| CH₂CH₃ | CH₂CH₃ | H | 5-Cl | S | |
| CH₂CH₃ | CH₂CH₃ | CH₃ | 5-Cl | O | |

TABLE 24

J = 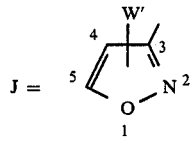

| R₁ | R₂ | R'' | W' | Properties |
|---|---|---|---|---|
| CH₃ | CH₃ | H | H | |
| CH₃ | CH₃ | CH₃ | H | |
| CH₂CH₃ | CH₂CH₃ | CH₃ | H | |
| CH₂CH₃ | CH₂CH₃ | H | H | |
| CH₂CH₃ | CH₂CH₃ | H | 4-CH₃ | |
| CH₂CH₃ | CH₂CH₃ | CH₃ | 4-CH₃ | |
| CH₂CH₃ | CH₂CH₃ | CH₂CH₃ | 4-CH₃ | |
| CH₃ | CH₃ | H | 4-CH₃ | |
| CH₃ | CH₃ | CH₃ | 4-CH₃ | |
| CH₃ | CH₃ | CH₂CH₃ | 4-CH₃ | |
| CH₃ | CH₃ | H | 4-CH₂CH₃ | |
| CH₃ | CH₃ | CH₃ | 4-CH₂CH₃ | |
| CH₂CH₃ | CH₂CH₃ | CH₃ | 4-CH₂CH₃ | |
| CH₂CH₃ | CH₂CH₃ | H | 4-CH₂CH₃ | |

TABLE 25

J = 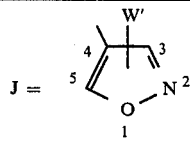

| R₁ | R₂ | R'' | W' | Properties |
|---|---|---|---|---|
| CH₂CH₃ | CH₂CH₃ | H | 3-CH₃ | |
| CH₂CH₃ | CH₂CH₃ | CH₃ | 3-CH₃ | |
| CH₃ | CH₃ | CH₃ | 3-CH₃ | |
| CH₃ | CH₃ | H | 3-CH₃ | |
| CH₃ | CH₃ | CH₂CH₃ | 3-Cl | |
| CH₃ | CH₃ | H | 3-Cl | |
| CH₂CH₃ | CH₂CH₃ | H | 3-Cl | |
| CH₂CH₃ | CH₂CH₃ | CH₃ | 3-Cl | |
| CH₂CH₃ | CH₂CH₃ | H | 3,5-(CH₃)₂ | |
| CH₂CH₃ | CH₂CH₃ | CH₃ | 3,5-(CH₃)₂ | |
| CH₂CH₃ | CH₂CH₃ | CH₂CH₃ | 3,5-(CH₃)₂ | |

TABLE 25-continued

J = 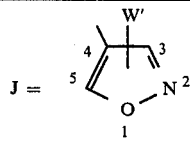

| R₁ | R₂ | R'' | W' | Properties |
|---|---|---|---|---|
| CH₃ | CH₃ | CH₃ | 3,5-(CH₃)₂ | |
| CH₃ | CH₃ | H | 3,5-(CH₃)₂ | |
| CH₃ | CH₃ | CH₂CH₃ | 3,5-(CH₃)₂ | |

TABLE 26

J = 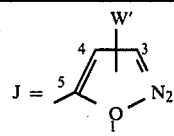

| R₁ | R₂ | R'' | W' | Properties |
|---|---|---|---|---|
| CH₃ | CH₃ | H | H | |
| CH₃ | CH₃ | CH₃ | H | |
| CH₂CH₃ | CH₂CH₃ | CH₃ | H | |
| CH₂CH₃ | CH₂CH₃ | H | H | |
| CH₂CH₃ | CH₂CH₃ | H | 3-CH₃ | |
| CH₂CH₃ | CH₂CH₃ | CH₃ | 3-CH₃ | |
| CH₂CH₃ | CH₂CH₃ | CH₂CH₃ | 3-CH₃ | |
| CH₃ | CH₃ | CH₂CH₃ | 3-CH₃ | |
| CH₃ | CH₃ | H | 3-CH₃ | |
| CH₃ | CH₃ | CH₃ | 3-CH₃ | |
| CH₃ | CH₃ | H | 3-Cl | |
| CH₃ | CH₃ | CH₃ | 3-Cl | |
| CH₃ | CH₃ | CH₂CH₃ | 3-Cl | |
| CH₂CH₃ | CH₂CH₃ | H | 3-Cl | |
| CH₂CH₃ | CH₂CH₃ | CH₃ | 3-Cl | |
| CH₂CH₃ | CH₂CH₃ | CH₂CH₃ | 3-Cl | |
| CH₂CH₃ | CH₂CH₃ | H | 3-OCH₃ | |
| CH₂CH₃ | CH₂CH₃ | CH₃ | 3-OCH₃ | |
| CH₃ | CH₃ | H | 3-OCH₃ | |
| CH₃ | CH₃ | CH₃ | 3-OCH₃ | |
| CH₃ | CH₃ | H | 4-CH₃ | |
| CH₃ | CH₃ | CH₃ | 4-CH₃ | |
| CH₂CH₃ | CH₂CH₃ | H | 4-CH₃ | |

TABLE 27

J = 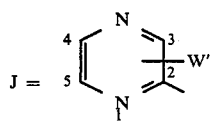

| R₁ | R₂ | R'' | W' | Properties |
|---|---|---|---|---|
| CH₃ | CH₃ | H | H | |
| CH₃ | CH₃ | CH₃ | H | |
| CH₃ | CH₃ | CH₂CH₃ | H | |
| CH₂CH₃ | CH₂CH₃ | H | H | |
| CH₂CH₃ | CH₂CH₃ | CH₃ | H | |
| CH₂CH₃ | CH₂CH₃ | CH₂CH₃ | H | |
| CH₂CH₃ | CH₂CH₃ | CH₂CH₃ | 3-Cl | |
| CH₂CH₃ | CH₂CH₃ | CH₃ | 3-Cl | |
| CH₂CH₃ | CH₂CH₃ | H | 3-Cl | |
| CH₃ | CH₃ | H | 3-Cl | |
| CH₃ | CH₃ | CH₃ | 3-Cl | |
| CH₃ | CH₃ | CH₂CH₃ | 3-Cl | |
| CH₃ | CH₃ | CH₂CH₃ | 3-Br | |
| CH₃ | CH₃ | H | 3-Br | |
| CH₂CH₃ | CH₂CH₃ | H | 3-Br | |
| CH₂CH₃ | CH₂CH₃ | CH₃ | 3-Br | |

TABLE 28

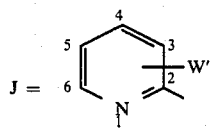

| R₁ | R₂ | R″ | W′ | Properties |
|---|---|---|---|---|
| CH₃ | CH₃ | H | H | white solid, m.p. 58-60° C. |
| CH₃ | CH₃ | CH₃ | H | |
| CH₃ | CH₃ | CH₂CH₃ | H | |
| CH₂CH₃ | CH₂CH₃ | H | H | |
| CH₂CH₃ | CH₂CH₃ | CH₃ | H | |
| CH₂CH₃ | CH₂CH₃ | CH₂CH₃ | H | |
| CH₂CH₃ | CH₂CH₃ | H | 6-F |  |
| CH₂CH₃ | CH₂CH₃ | CH₃ | 6-F |  |
| CH₃ | CH₃ | CH₃ | 6-F |  |
| CH₃ | CH₃ | H | 6-F |  |
| CH₂CH₃ | CH₂CH₃ | CH₃ | 6-Cl |  |
| CH₃ | CH₃ | H | 6-Cl |  |
| CH₂CH₃ | CH₂CH₃ | H | 6-Cl |  |
| CH₃ | CH₃ | CH₃ | 6-Cl |  |
| CH₃ | CH₃ | CH₃ | 6-CH₃ |  |
| CH₃ | CH₃ | H | 6-CH₃ |  |
| CH₂CH₃ | CH₂CH₃ | CH₂CH₃ | 6-CH₃ |  |
| CH₂CH₃ | CH₂CH₃ | H | 6-CH₃ |  |

TABLE 29

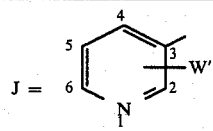

| R₁ | R₂ | R″ | W′ | Properties |
|---|---|---|---|---|
| CH₃ | CH₃ | H | 2-Cl | |
| CH₃ | CH₃ | CH₃ | 2-Cl | |
| CH₃ | CH₃ | CH₂CH₃ | 2-Cl | |
| CH₂CH₃ | CH₂CH₃ | H | 2-Cl | |
| CH₂CH₃ | CH₂CH₃ | CH₃ | 2-Cl | |
| CH₂CH₃ | CH₂CH₃ | CH₂CH₃ | 2-Cl | |
| CH₂CH₃ | CH₂CH₃ | H | 2-Br | |
| CH₂CH₃ | CH₂CH₃ | CH₃ | 2-Br | |
| CH₂CH₃ | CH₂CH₃ | CH₃ | 2-Br | |
| CH₃ | CH₃ | CH₃ | 2-Br | |
| CH₃ | CH₃ | H | 2-Br | |
| CH₃ | CH₃ | H | 2-F | |
| CH₃ | CH₃ | CH₃ | 2-F | |
| CH₂CH₃ | CH₂CH₃ | H | 2-F | |
| CH₂CH₃ | CH₂CH₃ | CH₃ | 2-F | |
| CH₂CH₃ | CH₂CH₃ | CH₃ | 2-CH₃ | |
| CH₃ | CH₃ | H | 2-CH₃ | |
| CH₃ | CH₃ | H | 2-CH₃ | |
| CH₃ | CH₃ | CH₂CH₃ | 2-CH₃ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE 30

|  | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, N.Y., 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 and Examples 1-4;

G. C. Klingman, "Weed Control as a Science", John Wiley and Sons, Inc., N.Y., 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 4

Wettable Powder 2-((2-methylphenyl)methoxy)-1,5,5,7-tetramethyl-4,8-dioxatricyclo[4.2.1.0$^{3,7}$]nonane, (1RS, 2RS), 75%; sodium alkylnaphthalenesulfonate, 2%; sodium ligninsulfonate, 2%; synthetic amorphous silica, 3%; kaolinite, 18%.

The ingredients are blended, hammer-milled until all the solids are essentially under 50 microns, reblended, and packaged.

EXAMPLE 5

Wettable Powder 2-((2-methylphenyl)methoxy)-1,5,5,7-tetramethyl-4,8-dioxatricyclo[4.2.1.0$^{3,7}$]nonane, (1RS, 2RS), 50%; sodium alkylnaphthalenesulfonate, 2%; low viscosity methyl cellulose, 2%; diatomaceous earth, 46%;

The ingredients are blended, coarsely hammer-milled and then air-milled to produce particles essentially all below 10 microns in diameter. The product is reblended before packaging.

EXAMPLE 6

Granule Wettable Powder of Example 4, 5%; attapulgite granules, 95%; (U.S. Pat. Ser. No. 20-40 mesh; 0.84-0.42 mm).

A slurry of wettable powder containing 25% solids is sprayed on the surface of attapulgite granules in a double-cone blender. The granules are dried and packaged.

EXAMPLE 7

Extruded Pellet 2-((2-methylphenyl)methoxy)-1,5,5,7-tetramethyl-4,8-dioxatricyclo[4.2.1.0$^{3,7}$]nonane, (1RS, 2RS), 25%; anhydrous sodium sulfate, 10%; crude calcium ligninsulfonate, 5%; sodium alkylnaphthalenesulfonate, 1%; calcium/magnesium bentonite, 59%;

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S. Ser. No. 20 sieve (0.84 mm openings). The granules held on a U.S. Ser. No. 40 sieve (0.42 mm openings) may be packaged for use and the fines recycled.

EXAMPLE 8

Low Strength Granule 2-((2-methylphenyl)methoxy)-1,5,5,7-tetramethyl-4,8-dioxatricyclo[4.2.1.0$^{3,7}$]nonane, (1RS, 2RS) 0.1%; attapulgite granules, 99.9%; (U.S. Ser. No. 20-40 mesh)

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 9

Granule 2-((2-methylphenyl)methoxy)-1,5,5,7-tetramethyl-4,8-dioxatricyclo[4.2.1.0$^{3,7}$]nonane, (1RS, 2RS), 80%; wetting agent, 1%; crude ligninsulfonate salt (containing 10% 5-20% of the natural sugars); attapulgite clay, 9%;

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 10

Aqueous Suspension 2-((2-methylphenyl)methoxy)-1,5,5,7-tetramethyl-4,8-dioxatricyclo[4.2.1.0$^{3,7}$]nonane, (1RS, 2RS), 40%; polyacrylic acid thickener, 0.3%; dodecylphenol polyethylene glycol ether, 0.5%; disodium phosphate, 1%; monosodium phosphate, 0.5%; polyvinyl alcohol, 1.0%; water, 56.7%.

The ingredients are blended and ground together in a sand mill to produce particles essentially all under 5 microns in size.

EXAMPLE 11

Solution 2-((2-methylphenyl)methoxy)-1,5,5,7-tetramethyl-4,8-dioxatricyclo[4.2.1.0$^{3,7}$]nonane, (1RS, 2RS), 5%; water, 95%.

The salt is added directly to the water with stirring to produce the solution, which may then be packaged for use.

EXAMPLE 12

High Strength Concentrate 2-((2-methylphenyl)methoxy)-1,5,5,7-tetramethyl-4,8-dioxatricyclo[4.2.1.0$^{3,7}$]nonane, (1RS, 2RS), 99%; silica aerogel, 0.5%; synthetic amorphous silica, 0.5%.

The ingredients are blended and ground in a hammer-mill to produce a material essentially all passing a U.S. Ser. No. 50 screen (0.3 mm opening). The concentrate may be formulated further if necessary.

EXAMPLE 13

Oil Suspension 2-((2-methylphenyl)methoxy)-1,5,5,7-tetramethyl-4,8-dioxatricyclo[4.2.1.0$^{3,7}$]nonane, (1RS, 2RS), 35%; blend of polyalcohol carboxylic 6%; esters and oil soluble petroleum sulfonates, xylene, 59%.

The ingredients are combined and ground together in a sand mill to produce particles essentially all below 5 microns. The product can be used directly, extended with oils, or emulsified in water.

EXAMPLE 14

Dust 2-((2-methylphenyl)methoxy)-1,5,5,7-tetramethyl-4,8-dioxatricyclo[4.2.1.0$^{3,7}$]nonane, (1RS, 2RS), 10%; attapulgite, 10%; Pyrophyllite, 80%.

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are highly active preemergent herbicides or plant growth regulatns. Many of them have utility for broad-spectrum preemergence control of grasses in crop and non-crop situations. Some of the compounds have utility for selective grass weed control in crops such as rice, soybeans, sugarbeets, and cotton. Alternatively, the subject compounds are useful to modify plant growth.

The rate of application for the compounds of the invention are determined by a number of factors, including the crop species involved, the types of weeds to be controlled, weather and climate, formulations selected, mode of application, amount of foliage present, etc. In general terms, the subject compounds should be applied at levels of around 0.10 to 20 kg/ha, the lower rates being suggested for use on lighter soils and/or those having a low organic matter content or for situations where only short-term persistence is required.

The compounds of the invention may be used in combination with any other commercial herbicide, non-limiting exampes of which are those of the sulfonylurea, triazine, triazole, uracil, urea, amide, diphenyl ether, carbamate, imidazolinone, cineole, and bipyridylium types. The compounds of this invention are particularly useful when combined with broadleaf herbicides to enlarge the spectrum of control.

The attached list exemplifies the compounds which may have utility in mixture with the instant compounds.

| Common Name | Chemical Name |
|---|---|
| acifluorfen | 5-[2-chloro-4-(trifluoromethyl)phenoxy]-2-nitrobenzoic acid |
| acrolein | acrolein |
| alachlor | 2-chloro-2',6'-diethyl-N—(methoxymethyl)-acetanilide |
| ametryn | 2-(ethylamino)-4-(isopropylamino)-6-methylthio)-s-triazine |
| amitrole | 3-amino-s-triazole |
| AMS | ammonium sulfamate |
| asulam | methyl sulfanilylcarbamate |
| atrazine | 2-chloro-4-(ethylamino)-6-(isopropylamino)-s-triazine |
| barban | 4-chloro-2-butynyl m-chlorocarbanilate |
| benefin | N—butyl-N—ethyl-α,α,α-trifluoro-2,6-dinitro-p-toluidine |
| bensulide | O,O—diisopropyl phosphorodithioate S—ester with N—(2-mercaptoethyl)-benzenesulfonamide |
| bentazon | 3-isopropyl-1H—2,1,3-benzothiadiazin-4(3H)—one 2,2-dioxide |
| benzipram | 3,5-dimethyl-N—(1-methylethyl)-N—(phenylmethyl)benzamide |
| benzoylprop | N—benzoyl-N—(3,4-dichlorophenyl)-DL-alaine |
| bifenox | methyl 5-(2,4-dichlorophenoxy)-2-nitrobenzoate |
| bromacil | 5-bromo-3-sec-butyl-6-methyluracil |
| bromoxynil | 3,5-dibromo-4-hydroxybenzonitrile |
| butachlor | N—(butoxymethyl)-2-chloro-2',6'-diethylacetanilide |
| butam | 2,2-dimethyl-N—(1-methylethyl)-N—(phenylmethyl)propanamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N—(1-methylpropyl)-2,6-dinitrobenzenamine |
| butylate | S—ethyl-diisobutylthiocarbamate |
| cacodylic acid | hydroxydimethylarsine oxide |
| carbetamide | D-N—ethyllactamide carbanilate (ester) |
| CDAA | N—N—diallyl-2-chloroacetamide |

-continued

| | Chemical Name |
|---|---|
| CDEC | 2-chloroallyl diethyldithiocarbamate |
| chlorbromuron | 3-(4-bromo-3-chlorophenyl)-1-methoxy-1-methylurea |
| chloroxuron | 3-[p-(p-chlorophenoxy)phenyl]-1,1-dimethylurea |
| chlorpropham | isopropyl m-chlorocarbanilate |
| chlorsulfuron | 2-chloro-N—[(4-methoxy-6-methyl-1,3,5-triazin-2-yl)aminocarbonyl]benzenesulfonamide |
| chlortoluron | N'—(3-chloro-4-methylphenyl-N',N'—dimethylurea |
| cisanilide | cis-2,5-dimethyl-N—phenyl-1-pyrrolidine-carboxamide |
| CMA | calcium methanearsonate |
| cyanazine | 2-[[4-chloro-6-(ethylamino)-s-triazin-2-yl]amino]-2-methylpropionitrile |
| cycloate | S—ethyl N—ethylthiocyclohexanecarbamate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N—[5-(2-chloro-1,1-dimethylethyl)-1,3,4-thiadiazol-2-yl] cyclopropanecarboxamide |
| cypromid | 3',4'-dichlorocyclopropanecarboxanilide |
| dalapon | 2,2-dichloropropionic acid |
| dazomet | tetrahydro-3,5-dimethyl-2H—1,3,5-thiadiazine-2-thione |
| DCPA | dimethyl tetrachloroterephthalate |
| desmetryn | 2-(isopropylamino)-4-(methylamino)-6-methylthio)-s-triazine |
| diallate | S—(2,3-dichloroallyl)diisopropylthiocarbamate |
| dicamba | 3,6-dichloro-o-anisic acid |
| dichlobenil | 2,6-dichlorobenzontrile |
| dichlorprop | 2-(2,4-dichlorophenoxy)propionic acid |
| diclofop | 2-[4-(2,4-dichlorophenoxy)phenoxy]-propanoic acid |
| diethatyl | N—(chloroacetyl)-N—(2,6-diethylphenyl)-glycine |
| difenzoquat | 1,2-dimethyl-3,5-diphenyl-1H—pyrazolium |
| dinitramine | N',N'—diethyl-α,α,α-trifluoro-3,5-dinitrotoluene-2,4-diamine |
| dinoseb | 2-sec-butyl-4,6-dinitrophenol |
| diphenamide | N,N—dimethyl-2,2-diphenylacetamide |
| dipropetryn | 2-(ethylthio)-4,6-bis(isopropylamino)-s-triazine |
| diquat | 6,7-dihydrodipyrido[1,2-a:2',1'-c]-pyrazinediium ion |
| diuron | 3-(3,4-dichlorophenyl)-1,1-dimethylurea |
| DSMA | disodium methanearsonate |
| endothall | 7-oxabicyclo[2.2.1]heptane-2,3-dicarboxylic acid |
| erbon | 2-(2,4,5-trichlorophenoxy)ethyl 2,2-dichloropropionate |
| ethafluralin | N—ethyl-N—(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| fenac | (2,3,6-trichlorophenyl)acetic acid |
| fenoxaprop ethyl | ethyl 2-(4-(6-chloro-2-benzoxazolyloxy)phenoxy)propanoate |
| fenuron | 1,1-dimethyl-3-phenylurea |
| fenuron TCA | 1,1-dimethyl-3-phenylurea mono(trichloroacetate) |
| flamprop | N—benzoyl-N—(3-chloro-4-fluorophenyl)-DL-alanine |
| fluchloralin | N—(2-chloroethyl)-2,6-dinitro-N—propyl-4-(trifluoromethyl)aniline |
| fluometuron | 1,1-dimethyl-3-(α,α,α-trifluoro-m-tolyl)-urea |
| fluorodifen | p-nitrophenyl α,α,α-trifluoro-2-nitro-p-tolyl ether |
| fluridone | 1-methyl-3-phenyl-5-[3-(trifluoromethyl)phenyl]-4(1H)—pyridinone |
| fomesafen | 5-(2-chloro-4-trifluoromethylphenoxy)-N—methylsulfonyl-2-nitrobenzamide |
| fosamine | ethyl hydrogen (aminocarbonyl)phosphonate |
| glyphosate | N—(phosphonomethyl)glycine |

-continued

| | Chemical Name |
|---|---|
| hexaflurate | potassium hexafluoroarsenate |
| hexazinone | 3-cyclohexyl-6-(dimethylamino)-1-methyl-1,3,5-triazine-2,4(1H,3H)—dione |
| imazaquin | 2-(4,5-dihydro-4-methyl-4-(1-methylethyl)-5-oxo-1H—imidazol-2-yl)-3-quinolinecarboxylic acid |
| ioxynil | 4-hydroxy-3,5-diiodobenzonitrile |
| isopropalin | 2,6-dinitro-N,N—dipropylcumidine |
| karbutilate | tert-butylcarbamic acid ester with 3-(m-hydroxyphenyl)-1,1-dimethylurea |
| lactofen | 1'-(carboethoxy)ethyl-5-(2-chloro-4-(trifluoromethyl)phenoxy)-2-nitrobenzoate |
| lenacil | 3-cyclohexyl-6,7-dihydro-1H—cyclopentapyrimidine-2,4(3H,5H)— dione |
| linuron | 3-(3,4-dichlorophenyl)-1-methoxy-1-methylurea |
| MAA | methanearsonic acid |
| MAMA | monoammonium methanearsonate |
| MCPA | [(4-chloro-o-tolyl)oxy]acetic acid |
| MCPB | 4-[(4-chloro-o-tolyl)oxy]butyric acid |
| mecoprop | 2-[(4-chloro-o-tolyl)oxy]propionic acid |
| mefluidide | N—[(2,4-dimethyl-5-[[(trifluoromethyl)sulfonyl]amino]phenyl]acetamide |
| methalpropalin | N—(2-methyl-2-propenyl)-2,6-dinitro-N—propyl-4-(trifluoromethyl)benzenamide |
| methabenzthiazuron | 1,3-dimethyl-3-(2-benzothiazolyl)urea |
| metham | sodium methyldithiocarbamate |
| methazole | 2-(3,4-dichlorophenyl)-4-methyl-1,2,4-oxadiazolidine-3,5-dione |
| methoxuron | N'—(3-chloro-4-methoxyphenyl)N,N—dimethylurea |
| metolachlor | 2-chloro-N—(2-ethyl-6-methylphenyl)-N—(2-methoxy-1-methylethyl)acetamide |
| metribuzin | 4-amino-6-tert-butyl-3-(methylthio)-as-triazine-5(4H)—one |
| metsulfuron methyl | 2-[[(4-methoxy-6-methyl-1,3,5-triazine-2-yl)aminocarbonyl]aminosulfonyl]benzoic acid, methyl ester |
| molinate | S—ethyl hexahydro-1H—azepine-1-carbothioate |
| monolinuron | 3-(p-chlorophenyl)-1-methoxy-1-methylurea |
| monuron | 3-(p-chlorophenyl)-1,1-dimethylurea |
| monuron TCA | 3-(p-chlorophenyl)-1,1-dimethylurea mono(trichloroacetate) |
| MSMA | monosodium methanearsonate |
| napropamide | 2-(α-naphthoxy)-N,N—diethylpropionamide |
| naptalam | N—1-naphthylphthalamic acid |
| neburon | 1-butyl-3-(3,4-dichlorophenyl)-1-methylurea |
| nitralin | 4-(methylsulfonyl)-2,6-dinitro-N,N—dipropylaniline |
| nitrofen | 2,4-dichlorophenyl p-nitrophenyl ether |
| nitrofluorfen | 2-chloro-1-(4-nitrophenoxy)-4-(trifluoromethyl)benzene |
| norea | 3-(hexahydro-4,7-methanoindan-5-yl)-1,1-dimethylurea |
| norflurazon | 4-chloro-5-(methylamino)-2-(α,α,α-trifluoro-m-tolyl)-3(2H)—pyridazinone |
| oryzalin | 3,4-dinitro-N,N—dipropylsulfanilamide |
| oxadiazon | 2-tert-butyl-4-(2,4-dichloro-5-isopropoxyphenyl)Δ²-1,3,4-oxadiazolin-5-one |
| oxyfluorfen | 2-chloro-1-(3-ethoxy-4-nitrophenoxy)-4-(trifluoromethyl)benzene |
| paraquat | 1,1'-dimethyl-4,4'-bipyridinium ion |
| PBA | chlorinated benzoic acid |
| pendimethalin | N—(1-ethylpropyl)-3,4-dimethyl-2,6-dinitrobenzenamine |
| perfluidone | 1,1,1-trifluoro-N—[2-methyl-4-(phenylsulfonyl)phenyl]methanesulfonamide |
| picloram | 4-amino-3,5,6-trichloropicolinic acid |
| procyazine | 2-[[4-chloro-6-(cyclopropylamino)-1,3,5-triazine-2-yl]amino]-2-methylpropanenitrile |
| profluralin | N—(cyclopropylmethyl)-α,α,α-trifluoro-2,6-dinitro-N—propyl-p-toluidine |
| prometon | 2,4-bis(isopropylamino)-6-methoxy-s-triazine |

-continued

| | Chemical Name |
|---|---|
| prometryn | 2,4-bis(isopropylamino)-6-(methylthio)-s-triazine |
| pronamide | 3,5-dichloro N—(1,1-dimethyl-2-propynyl)benzamide |
| propachlor | 2-chloro-N—isopropylacetanilide |
| propanil | 3',4'-dichloropropionalide |
| propazine | 2-chloro-4,6-bis(isopropylamino)-s-triazine |
| propham | isopropyl carbanilate |
| prosulfalin | N—[[4-(dipropylamino)-3,5-dinitrophenyl]sulfonyl]-S,S—dimethylsulfilimine |
| prynachlor | 2-chloro-N—(1-methyl-2-propynyl)acetanilide |
| quinofop ethyl | 2-[4-(6-chloroquinoxalin-2-yloxy)phenoxypropanoic acid, ethyl ester |
| secbumeton | N—ethyl-6-methoxy-N'(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexene-1-one |
| siduron | 1-(2-methylcyclohexyl)-3-phenylurea |
| simazine | 2-chloro-4,6-bis(ethylamino)-s-triazine |
| simetryn | 2,4-bis(ethylamino)-6-(methylthio)-s-triazine |
| supriox | 2-[1-(2,5-dimethylphenyl)ethylsulfonyl]-pyridine-N—oxide |
| TCA | trichloroacetic acid |
| tebuthiuron | N—[5-(1,1-dimethylethyl)-1,3,4-thiadiazol-2-yl]-N,N'—dimethylurea |
| terbacil | 3-tert-butyl-5-chloro-6-methyluracil |
| terbuchlor | N—(butoxymethyl)-2-chloro-N—[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | 2-(tert-butylamino)-4-(ethylamino)-6-(methylthio)-s-triazine |
| tetrafluron | N,N—dimethyl-N'—[3-(1,1,2,2-tetrafluoroethoxy)phenyl]urea |
| thiobencarb | S—[(4-chlorophenyl)methyl] diethylcarbamothioate |
| triallate | S—(2,3,3-trichloroallyl)diisopropylthiocarbamate |
| trifluralin | α,α,α-trifluoro-2,6-dinitro-N,N—propyl-p-toluidine |
| trimeturon | 1-(p-chlorophenyl)-2,3,3-trimethylpseudourea |
| vernolate | S—propyl dipropylthiocarbamate |
| 2,3,6-TBA[b] | ethyl 5-[2-chloro-4-(trifluoromethyl)-phenoxy]-2-nitrobenzoic acid 2,3,6-trichlorobenzoic acid |
| 2,4-D | (2,4-dichlorophenoxy)acetic acid |
| 2,4-DB | 4-(2,4-dichlorophenoxy)butyric acid |
| 2,4-DEP | tris[2-(2,4-dichlorophenoxy)ethyl] phosphite |

| Trade Name or Code Number | |
|---|---|
| "Cinch" | exo-1-methyl-4-(1-methylethyl)-2-[(2-methylphenyl)methoxy]-7-oxabicyclo-[2.2.1]heptane |
| AC 263,499 | 2-[4,5-dihydro-4-methyl-4-(1-methylethyl)-5-oxo-1H—imidazol-2-yl]-5-ethyl-3-pyridinecarboxylic acid |
| Harmony ™ | 3-[[(4-methoxy-6-methyl-1,3,5-triazin-2-yl)aminocarbonyl]aminosulfonyl]-2-thiophenecarboxylic acid, methyl ester |
| PPG-1013 | 5-(2-chloro-4-(trifluoromethyl)phenoxy)-2-nitroacetophenone oxime-O—acetic acid, methyl ester |
| DOWCO 453 ME | 2-(4-(3-chloro-5-trifluoromethylpyridin-2-yloxy)phenoxy)propanoic acid, methyl ester |
| FMC 57020 | 2-(2'-chlorophenyl)methyl-4,4-dimethyl-3-isoxazolidinone |
| AC 222,293 | 6-(4-isopropyl-4-methyl-5-oxo-2-imidazolin-2-yl)-m-toluic acid, methyl ester and 6-(4-isopropyl-4-methyl-5- |

| | Chemical Name |
|---|---|
| | oxo-2-imidazolin-2-yl-p-toluic acid, methyl ester |
| AC 252,925 | 2-(4-isopropyl-4-methyl-5-oxo-2-imidazolin-2-yl)nicotinic acid with isopropyl amine (1:1) |
| Express ® | 2-[[N—(4-methoxy-6-methyl-1,3,5-triazine-2-yl)-N—methylaminocarbonyl]-aminosulfonyl]benzoic acid, methyl |
| bromofenoxium | 3,5-dibromo-4-hydroxybenzaldehyde-O—2',4'-dinitrophenyl)oxime |
| DNOC | 2-methyl-4,6-dinitrophenol |
| isoproturon | N—(4-isopropylphenyl)-N',N'—dimethyl-urea |
| quizalofop | 2-[4,5-dihydro-4-methyl-e-(1-methyl)-ethyl]-5-oxo-1H—imidazol-2-yl]-3-quinolinecarboxylic acid |
| — | 2-(4-(3-chloro-5-trifluoromethylpyridin-2-yl-oxy)phenoxy)propanoic acid, methyl ester |
| Command ™ | 2-(2'-chlorophenyl)methyl-4,4-dimethyl-3-isoxazolidinone |
| — | 3-methyl-6-[4,5-dihydro-5-methyl-5-(1-methylethyl)-4-oxo-1H—imidazol-2-yl]-benzoic acid, methyl ester |
| — | 4-chloro-2-[[(4-methoxy-6-methyl, 1,3,5-triazin-2-yl)aminocarbonyl]amino-sulfonyl]benzoic acid, (1-methyl-ethyl)ester |

The herbicidal properties of the subject compounds were discovered in a number of greenhouse tests. The test procedures and results follow.

TABLE 31

Biological Table

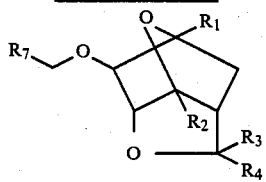

| CMPD | $R_1$ | $R_2$ | $R_3$ | $R_4$ | $R_7$ |
|---|---|---|---|---|---|
| 1 | $CH_3$ | $CH_3$ | $CH_3$ | $CH_3$ | Ph |
| 2 | $CH_3$ | $CH_3$ | $CH_3$ | $CH_3$ | 2-$CH_3$—Ph |
| 3 | $CH_3$ | $CH_3$ | $CH_3$ | $CH_3$ | 2-Cl—Ph |
| 4 | $CH_3$ | $CH_3$ | $CH_3$ | $CH_3$ | 2-F—Ph |
| 5 | $CH_3$ | $CH_3$ | $CH_3$ | $CH_3$ | 2-pyridyl |
| 6 | $CH_3$ | $CH_3$ | $CH_3$ | $CH_3$ | 2,6-di-Cl—Ph |
| 7 | $CH_3$ | $CH_3$ | H | H | 2-F—Ph |
| 8 | $CH_3$ | $CH_3$ | H | H | Ph |
| 9 | $CH_3$ | $CH_3$ | $CH_2CH_3$ | $CH_2CH_3$ | PH |

TABLE 31-continued

Biological Table

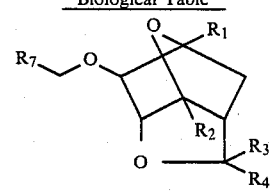

| CMPD | $R_1$ | $R_2$ | $R_3$ | $R_4$ | $R_7$ |
|---|---|---|---|---|---|
| 10 | $CH_3$ | $CH_3$ | $CH_2CH_3$ | $CH_2CH_3$ | 2-F—Ph |
| 11 | $CH_3$ | $CH_3$ | H | H | 2-F—6-Cl—Ph |
| 12 | $CH_3$ | $CH_3$ | $CH_2CH_3$ | $CH_2CH_3$ | 2-$CH_3$—Ph |
| 13 | $CH_3$ | $CH_3$ | $CH_2CH_3$ | $CH_2CH_3$ | 2,3-di-F—Ph |
| 14 | $CH_3$ | $CH_3$ | $CH_2CH_3$ | $CH_2CH_3$ | 2,6-di-F—Ph |
| 15 | $CH_3$ | $CH_3$ | $CH_2CH_3$ | $CH_2CH_3$ | 2-Cl—Ph |
| 16 | $CH_3$ | $CH_3$ | $CH_2CH_3$ | $CH_2CH_3$ | 2-Cl—6-F—Ph |

Test A

Seeds of crabgrass (Digitaria sp.), barnyard-grass (Echinochloa crus-galli), giant foxtail (Setaria faberii), wild oats (Avena fatua), cheatgrass (Bromus secalinus). velvetleaf (Abutilon threophrasti), morningglory (Ipomoea sp.), cocklebur (Xanthium pennsylvanicum), sorghum, corn, soybean, sugarbeet, cotton, rice, barley, wheat and purple nutsedge (Cyperus rotundus) were planted and treated pre-emergence with the chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, wherupon all species were compared to controls and visually rated for response to treatment. The ratings, summarized in Table A, are based on a numerical scale extending from 0=no injury, to 10=complete kill. The accompanying descriptive symbols have the following meanings:

C=chlorosis or necrosis;
B=burn;
D=defoliation;
E=emergence inhibition;
G=growth retardation;
H=formative effects;
U=unusual pigmentation;
X=axillary stimulation; and
S=albinism; and
Y=abscised buds or flowers.

TABLE A

| RATE = KG/HA | CMPD 1 0.4 | CMPD 2 0.4 | CMPD 3 0.4 | CMPD 4 0.4 | DMPD 5 0.4 | CMPD 6 0.4 | CMPD 7 0.4 | CMPD 8 0.4 |
|---|---|---|---|---|---|---|---|---|
| | | | POSTEMEGENCE | | | | | |
| COTTON | 0 | 0 | 0 | 0 | 0 | 0 | 0 | 0 |
| MORNINGGLORY | 0 | 0 | 0 | 0 | 0 | 0 | 0 | 0 |
| COCKLEBUR | 2B | 2B | 1H | 1B,1H | 1H | 1B | 1C | 0 |
| NUTSEDGE | 0 | 0 | 7G | — | 0 | 0 | 3C,8H | 0 |
| CRABGRASS | 8C | 3C,7G | 2G | 5C,8G | 3C,6G | 0 | 3C,9H | 2S,6G |
| BARNYARDGRASS | 5C | 3C,6G | 2C,5H | 4C,9H | 3G | 0 | 2C,4H | 0 |
| WILD OATS | 0 | 0 | 0 | 0 | 0 | 0 | 0 | 0 |
| WHEAT | 8G | 0 | 0 | 6G | 0 | 0 | 6G | 0 |
| CORN | 3C,5G | 4G | 2G | 2C,2H | 0 | 0 | 3C,6H | 2C |
| SOYBEANS | 1B | 0 | 1H | 0 | 1C,1H | 0 | 3C,6H | 1S,3H |
| RICE | 0 | 0 | 2G | 0 | 0 | 0 | 0 | 0 |
| SORGHUM | 0 | 0 | 2C,7G | 0 | 2G | 0 | 0 | 0 |
| CHEAT GRASS | 0 | 0 | 0 | 0 | 0 | 0 | 0 | 0 |
| SUGARBEETS | 0 | 0 | 0 | 0 | 3G | 0 | 4H | 0 |
| VELVETLEAF | 2H | 2G | 3G | 1C | 0 | — | 0 | 0 |
| GIANT FOXTAIL | 3C,8G | 3C,6G | 2G | 4C,8H | 0 | 0 | 2C,9H | 2S,7G |
| BARLEY | 1C | 0 | 0 | 0 | 0 | 0 | 0 | 0 |

TABLE A-continued

PREEMERGENCE

| | | | | | | | | |
|---|---|---|---|---|---|---|---|---|
| COTTON | 0 | 0 | 0 | 2G | 0 | 0 | 0 | 0 |
| MORNINGGLORY | 0 | 0 | 0 | 0 | 1C | 0 | 0 | 2G |
| COCKLEBUR | 0 | 0 | — | 0 | 0 | 0 | 1C | 0 |
| NUTSEDGE | 10E | 9G | 9G | 4C,9G | 0 | 0 | 7G | 2C,4G |
| CRABGRASS | 3C,9G | 3C,9G | 3C,9G | 5C,9G | 3C,5G | 2C,4G | 2C,9G | 9G |
| BARNYARDGRASS | 3C,9H | 3C,9H | 5C,9H | 9H | 3G | 4G | 9H | 3S,8H |
| WILD OATS | 3G | 0 | 5G | 3C,5G | 0 | 0 | 3G | 0 |
| WHEAT | 8G | 7G | 6G | 9G | 0 | 0 | 5G | 0 |
| CORN | 3C,8G | 2C,5G | 0 | 3C,7H | 2C | 0 | 6C | 2S,7G |
| SOYBEANS | 0 | 0 | 0 | 0 | 0 | 0 | 2C,5G | 2C |
| RICE | 0 | 0 | 0 | 0 | 0 | 0 | 2C,3H | 1C |
| SORGHUM | 3C,5G | 2C,7G | 0 | 3C,8H | 0 | 0 | 4C,8H | 1C |
| CHEAT GRASS | 8G | 5G | 3G | 7G | 0 | 0 | 2G | 0 |
| SUGARBEETS | 0 | 0 | 0 | 0 | 9C | 0 | 0 | 2G |
| VELVETLEAF | 3H | 3C,5H | 2C,5H | 2H | 2G | | 2C,6H | 2S,5H |
| GIANT FOXTAIL | 3C,8G | 3C,8G | 4C,8H | 5C,9H | 9H | 3C,8G | 3C,9H | 8H |
| BARLEY | 6G | 2C,5G | 0 | 8G | 0 | 0 | 8G | 7G |

| | CMPD 9 | CMPD 10 | CMPD 11 | CMPD 12 | CMPD 13 | CMPD 14 | CMPD 15 | CMPD 16 |
|---|---|---|---|---|---|---|---|---|
| RATE = KG/HA | 0.4 | 0.4 | 0.4 | 0.4 | 0.4 | 0.4 | 0.4 | 0.4 |

POSTEMERGENCE

| | | | | | | | | |
|---|---|---|---|---|---|---|---|---|
| COTTON | 0 | 1C,1H | 2H | 0 | 0 | 7H | 0 | 6G |
| MORNINGGLORY | 0 | 0 | 1H | 0 | 0 | 0 | 0 | 0 |
| COCKLEBUR | 0 | 0 | 4H | 1B | 1B | 1B | 2B | 3B |
| NUTSEDGE | 0 | 0 | 0 | 0 | 0 | 0 | 0 | 0 |
| CRABGRASS | 0 | 0 | 3C,5H | 0 | 2C | 3S,5G | 0 | 2B |
| BARNYARDGRASS | 3C,8H | 3C,8H | 0 | 0 | 0 | 3C,7H | 0 | 2G |
| WILD OATS | 0 | 0 | 0 | 0 | 0 | 0 | 0 | 0 |
| WHEAT | 3G | 3G | 5G | 0 | 0 | 3G | 0 | 0 |
| CORN | 2G | 3G | 2C,3H | 0 | 0 | 3C,3H | 0 | 0 |
| SOYBEANS | 0 | 1H | 6H | 0 | 0 | 3H | 0 | 0 |
| RICE | 0 | 2G | 0 | 0 | 0 | 0 | 0 | 0 |
| SORGHUM | 0 | 0 | 0 | 0 | 0 | 0 | 0 | 0 |
| CHEAT GRASS | 0 | 0 | 0 | 0 | 0 | 0 | 0 | 0 |
| SUGARBEETS | 0 | 0 | 0 | 0 | 0 | 2H | 0 | 0 |
| VELVETLEAF | 0 | 0 | 6H | 1H | 1H | 1H | 2G | 5G |
| GIANT FOXTAIL | 0 | 2G | 9H | 0 | 0 | 0 | 0 | 0 |
| BARLEY | 2G | 3G | 0 | 0 | 0 | 7G | 0 | 0 |

PREEMERGENCE

| | | | | | | | | |
|---|---|---|---|---|---|---|---|---|
| COTTON | 0 | 0 | 0 | 0 | 0 | 2G | 3G | 0 |
| MORNINGGLORY | 0 | 0 | 2G | 0 | 0 | 0 | 0 | 0 |
| COCKLEBUR | 0 | 0 | 0 | 0 | 0 | 0 | 0 | 0 |
| NUTSEDGE | 0 | 0 | 10E | 4G | 0 | 10E | 0 | 3G |
| CRABGRASS | 9H | 3C,8H | 3C,9H | 4C,9G | 3C,8G | 5C,9H | 2S,5G | 3S,9G |
| BARNYARDGRASS | 9H | 9H | 10H | 4C,8H | 5C,9H | 9H | 2S,8H | 3S,8H |
| WILD OATS | 0 | 2G | 0 | 0 | 2G | 4G | 0 | 0 |
| WHEAT | 3G | 2G | 0 | 0 | 2G | 3G | 0 | 0 |
| CORN | 3C,7H | 3C,7G | 3C,5H | 0 | 2G | 2C,3G | 0 | 0 |
| SOYBEANS | 0 | 0 | 3C,8H | 0 | 0 | 0 | 0 | 0 |
| RICE | 3C,6G | 3G | 0 | 0 | 0 | 3G | 0 | 0 |
| SORGHUM | 3C,7G | 7G | 0 | 0 | 0 | 5G | 0 | 0 |
| CHEAT GRASS | 3G | 8G | 2G | 8G | 7G | 8G | 0 | 0 |
| SUGARBEETS | 1H | 2H | 0 | 0 | 0 | 0 | 0 | 0 |
| VELVETLEAF | 1H | 0 | 5H | 2H | 0 | 3H | 0 | 0 |
| GIANT FOXTAIL | 9H | 9H | 4C,9H | 4C,9H | 9H | 4C,9H | 2S,8G | 3S,9G |
| BARLEY | 2G | 0 | 0 | 0 | 0 | 2G | 0 | 0 |

Test B

Postemergence

Three round pans (25 cm diameter by 12.5 cm deep) were filled with Sassafras sandy loam soil. One pan was planted with nutsedge (*Cyperus rotundus*) tubers, crabgrass (*Digitaria sanguinalis*), sicklepod (*Cassia obtusifolia*), jimsonweed (*Datura stramonium*), velvetleaf (*Abutilon theophrasti*), lambsquarters (*Chenopodium album*), rice (*Oryza sativa*) and teaweed (*Sida spinosa*). The second pot was planted with green foxtail (*Setaria viridis*), cocklebur (*Xantium pensylvanicum*), morningglory (*Ipomoea hederacea*), cotton (*Gossypium hirsutum*), johnsongrass (*Sorghum halepense*), barnyardgrass (*Echinochloa crusgalli*), corn (*Zea mays*), soybean (*Glycine max*) and giant foxtail (*Setaria faberi*). The third pot was planted with wheat (*Triticum aestivum*), barley (*Hordeum vulgare*), wild buckwheat (*Polgonum convolvulus L.*), cheatgrass (*Bromus secalinus L.*), sugarbeet (*Beta vulgaris*), wild oats (*Avena fatua*), common chickweed (*Stellaria media*), blackgrass (*Alopecurus myosuroides*), and rape (*Brassica napus*). The plants were grown for approximately fourteen days, then sprayed postemergence with the chemicals dissolved in a non-phytotoxic solvent.

Preemergence

Three round pans (25 cm diameter by 12.5 cm deep) were filled with Sassafras sandy loam soil. One pan was planted with nutsedge tubers, crabgrass, sicklepod, jimsonweed, velvetleaf, lambsquarters, rice and teaweed. The second pot was planted with green foxtail, cocklebur, morningglory, cotton, johnsongrass, barnyardgrass, corn, soybean and giant foxtail. The third pot was planted with wheat, barley, wild buckwheat, cheatgrass, sugarbeet, wild oat, viola, blackgrass and rape. The three pans were sprayed preemergence with the chemicals dissolved in a non-phytotoxic solvent.

Treated plants and controls were maintained in the greenhouse for 24 days, then all rated plants were compared to controls and visually rated for plant response.

Response ratings are based on a scale of 0 to 100 where 0=no effect and 100=complete control. A dash (—) response means no test.

Response ratings are contained in Table B.

maining pots were planted with barnyardgrass (*Echinochloa crus-galli*) seeds and sprouted tubers of water chestnut (*Elocharis* spp.). These weeds all represent major rice weeds or genera of weeds important in rice. Three to four days after planting, the water level was raised to 3 cm (about 1200 ml/pot) and maintained at this level throughout the test. Chemical treatments

TABLE B

| | CMPD 1 | | | | CMPD 2 | | | | CMPD 3 | | | | CMPD 4 | | | |
|---|---|---|---|---|---|---|---|---|---|---|---|---|---|---|---|---|
| RATE = G/HA | 0500 | 0250 | 0125 | 0062 | 0500 | 0250 | 0125 | 0062 | 0500 | 0250 | 0125 | 0062 | 0500 | 0250 | 0125 | 0062 |
| | | | | | PREEMERGENCE | | | | | | | | | | | |
| GIANT FOXTAIL | 70 | 50 | 30 | 0 | 100 | 90 | 70 | 60 | 90 | 70 | 50 | 30 | 100 | 90 | 80 | 70 |
| VELVETLEAF | 30 | — | 0 | 0 | 90 | 60 | 30 | 0 | 30 | 0 | 0 | 0 | 60 | 30 | 0 | 0 |
| SUGARBEETS | 0 | 0 | 0 | 0 | 0 | 0 | 0 | 0 | 0 | 0 | 0 | 0 | 0 | 0 | 0 | 0 |
| CRABGRASS | 100 | 90 | 80 | 50 | 100 | 90 | 80 | 50 | 90 | 70 | 50 | 30 | 100 | 100 | 90 | 80 |
| PRICKLY SIDA | 30 | 0 | 0 | 0 | 30 | 0 | 0 | 0 | 30 | 0 | 0 | 0 | 30 | 0 | 0 | 0 |
| JIMSONWEED | 30 | 0 | 0 | 0 | 30 | 0 | 0 | 0 | 30 | 0 | 0 | 0 | 30 | 0 | 0 | 0 |
| RICE | 50 | 0 | 0 | 0 | 30 | 0 | 0 | 0 | 0 | 0 | 0 | 0 | 0 | 0 | 0 | 0 |
| COCKLEBUR | 30 | 0 | 0 | 0 | 0 | 0 | 0 | 0 | 50 | 30 | 0 | 0 | 30 | 0 | 0 | 0 |
| COTTON | 0 | 0 | 0 | 0 | 0 | 0 | 0 | 0 | 0 | 0 | 0 | 0 | 0 | 0 | 0 | 0 |
| SOYBEANS | 0 | 0 | 0 | 0 | 0 | 0 | 0 | 0 | 20 | 0 | 0 | 0 | 0 | 0 | 0 | 0 |
| BARNYARDGRASS | 90 | 70 | 50 | 30 | 100 | 90 | 70 | 60 | 80 | 50 | 30 | 0 | 100 | 90 | 80 | 60 |
| WILD OATS | 0 | 0 | 0 | 0 | 0 | 0 | 0 | 0 | 30 | 0 | 0 | 0 | 30 | 0 | 0 | 0 |
| MORNINGGLORY | 70 | 60 | 50 | 30 | 0 | 0 | 0 | 0 | 30 | 0 | 0 | 0 | 30 | 0 | 0 | 0 |
| WHEAT | 0 | 0 | 0 | 0 | 50 | 30 | 0 | 0 | 0 | 0 | 0 | 0 | 60 | 30 | 0 | 0 |
| SICKLEPOD | 0 | 0 | 0 | 0 | 30 | 0 | 0 | 0 | 0 | 0 | 0 | 0 | 0 | 0 | 0 | 0 |
| JOHNSONGRASS | 70 | 50 | 30 | 0 | 70 | 60 | 50 | 30 | 70 | 50 | 30 | 0 | 90 | 80 | 70 | 60 |
| NUTSEDGE | 30 | 0 | 0 | 0 | 80 | 30 | 0 | 0 | 0 | 0 | 0 | 0 | 50 | 30 | 20 | — |
| CORN | 60 | 0 | 0 | 0 | 50 | 0 | 0 | 0 | 0 | 0 | 0 | 0 | 20 | 0 | 0 | 0 |
| WILD BUCKWHEAT | 30 | 0 | 0 | 0 | 0 | 0 | 0 | 0 | 0 | 0 | 0 | 0 | 30 | 0 | 0 | 0 |
| BLACKGRASS | 100 | 80 | 50 | 30 | 80 | 70 | 50 | 30 | 70 | 50 | 30 | 0 | 90 | 80 | 50 | 30 |
| RAPE | 0 | 0 | 0 | 0 | 0 | 0 | 0 | 0 | 0 | 0 | 0 | 0 | 0 | 0 | 0 | 0 |
| BARLEY | 30 | 0 | 0 | 0 | 60 | 30 | 0 | 0 | 0 | 0 | 0 | 0 | 70 | 30 | 0 | 0 |
| GREEN FOXTAIL | 60 | 50 | 30 | 0 | 70 | 50 | 30 | 0 | 70 | 50 | 30 | 0 | 80 | 60 | 50 | 30 |
| CHEAT GRASS | 80 | 50 | 30 | 0 | 70 | 50 | 30 | 0 | 50 | 30 | 0 | 0 | 80 | 70 | 50 | 30 |
| LAMBSQUARTER | 0 | 0 | 0 | 0 | 90 | 85 | 80 | 70 | 60 | 30 | 0 | 0 | 50 | 30 | 0 | 0 |
| CHICKWEED | 90 | 70 | 50 | 30 | 50 | 30 | 0 | 0 | 0 | 0 | 0 | 0 | 50 | 30 | 0 | 0 |
| | CMPD 1 | | | | CMPD 2 | | | | CMPD 3 | | | | CMPD 4 | | | |
| RATE = G/HA | 0500 | 0250 | 0125 | 0062 | 0500 | 0250 | 0500 | 0250 | 0125 | 0062 | | | 0500 | 0250 | 0125 | 0062 |
| | | | | | POSTEMERGENCE | | | | | | | | | | | |
| GIANT FOXTAIL | 80 | 60 | 30 | 0 | 30 | 0 | 30 | 0 | 0 | 0 | | | 60 | 30 | 0 | 0 |
| VELVETLEAF | 60 | 30 | 0 | 0 | 70 | 30 | 30 | 0 | 0 | 0 | | | 0 | 0 | 0 | 0 |
| SUGARBEETS | 60 | 30 | 0 | 0 | 0 | 0 | 0 | 0 | 0 | 0 | | | 0 | 0 | 0 | 0 |
| CRABGRASS | 30 | 0 | 0 | 0 | 50 | 30 | 0 | 0 | 0 | 0 | | | 30 | 0 | 0 | 0 |
| PRICKLY SIDA | 30 | 0 | 0 | 0 | 0 | 0 | 0 | 0 | 0 | 0 | | | 0 | 0 | 0 | 0 |
| JIMSONWEED | 0 | 0 | 0 | 0 | 0 | 0 | 0 | 0 | 0 | 0 | | | 30 | 0 | 0 | 0 |
| RICE | 0 | 0 | 0 | 0 | 0 | 0 | 0 | 0 | 0 | 0 | | | 0 | 0 | 0 | 0 |
| COCKLEBUR | 30 | 0 | 0 | 0 | 30 | 0 | 0 | 0 | 0 | 0 | | | 30 | 0 | 0 | 0 |
| COTTON | 0 | 0 | 0 | 0 | 0 | 0 | 0 | 0 | 0 | 0 | | | 0 | 0 | 0 | 0 |
| SOYBEANS | 0 | 0 | 0 | 0 | 0 | 0 | 0 | 0 | 0 | 0 | | | 0 | 0 | 0 | 0 |
| BARNYARDGRASS | 50 | 30 | 0 | 0 | 30 | 0 | 0 | 0 | 0 | 0 | | | 60 | 30 | 0 | 0 |
| WILD OATS | 0 | 0 | 0 | 0 | 0 | 0 | 0 | 0 | 0 | 0 | | | 0 | 0 | 0 | 0 |
| MORNINGGLORY | 0 | 0 | 0 | 0 | 0 | 0 | 0 | 0 | 0 | 0 | | | 0 | 0 | 0 | 0 |
| WHEAT | 0 | 0 | 0 | 0 | 0 | 0 | 0 | 0 | 0 | 0 | | | 60 | 30 | 0 | 0 |
| SICKLEPOD | 0 | 0 | 0 | 0 | 0 | 0 | 0 | 0 | 0 | 0 | | | 0 | 0 | 0 | 0 |
| JOHNSONGRASS | 0 | 0 | 0 | 0 | 0 | 0 | 30 | 0 | 0 | 0 | | | 0 | 0 | 0 | 0 |
| NUTSEDGE | 0 | 0 | 0 | 0 | 0 | 0 | 0 | 0 | 0 | 0 | | | 0 | 0 | 0 | 0 |
| CORN | 0 | 0 | 0 | 0 | 0 | 0 | 0 | 0 | 0 | 0 | | | 0 | 0 | 0 | 0 |
| WILD BUCKWHEAT | 50 | 30 | 0 | 0 | 0 | 0 | 0 | 0 | 0 | 0 | | | 0 | 0 | 0 | 0 |
| BLACKGRASS | 50 | 30 | 0 | 0 | 30 | 0 | 70 | 60 | 50 | 30 | | | 90 | 60 | 30 | 0 |
| RAPE | 90 | 70 | 50 | 30 | 30 | 0 | 50 | 30 | 0 | 0 | | | 30 | 0 | 0 | 0 |
| BARLEY | 0 | 0 | 0 | 0 | 0 | 0 | 0 | 0 | 0 | 0 | | | 60 | 30 | 0 | 0 |
| GREEN FOXTAIL | 30 | 0 | 0 | 0 | 0 | 0 | 0 | 0 | 0 | 0 | | | 30 | 0 | 0 | 0 |
| CHEAT GRASS | 0 | 0 | 0 | 0 | 0 | 0 | 0 | 0 | 0 | 0 | | | 0 | 0 | 0 | 0 |
| LAMBSQUARTER | — | — | 0 | 0 | 50 | 30 | 0 | 0 | 0 | 0 | | | 0 | 0 | 0 | 0 |
| CHICKWEED | 50 | 0 | 0 | 0 | 0 | 0 | 0 | 0 | 0 | 0 | | | 0 | 0 | 0 | 0 |

Test C

Sixteen cm diameter Airlite plastic pots were partially filled with Tama silt loam soil and the soil saturated with water. Japonica and Indica rice seedlings at the 2.0 to 2.5 leaf stage were transplanted into ⅓ of the pots. Into another third of the pots were transplanted seedling or sprouted tubers of water plantain (*Alisma trivale*), Scripus (*Scirpus paludosus*), Cyperus (*Cyperus esculentus*), and arrowhead (*Sagittaria* spp.). The rewere applied directly to the paddy water, withint 24 hours of raising the water, after being formulated in a non-phytottoxic solvent. The pots were maintained in the greenhouse. Rate of application and plant response ratings made 21 days after treatment are summarized in Table C.

TABLE C

| SOIL TYPE TAMARA | RATE = G/HA | | | | |
|---|---|---|---|---|---|
| | 1000 | 0500 | 0250 | 0125 | 0064 |
| CMPD 1 | | | | | |
| BARNYARDGRASS | 95 | 80 | 60 | 0 | 0 |
| WATERCHESTNUT | 0 | 0 | 0 | 0 | 0 |
| ARROWHEAD | 0 | 0 | 0 | 0 | 0 |
| SCIRPUS | 0 | 0 | 0 | 0 | 0 |
| YELLOW NUTSEDGE | 0 | 0 | 0 | 0 | 0 |
| WATER PLAINTAIN | 0 | 0 | 0 | 0 | 0 |
| RICE JAPONICA EFF | 60 | 30 | 0 | 0 | 0 |
| RICE INDICA EFF | 70 | 30 | 0 | 0 | 0 |
| CMPD 2 | | | | | |
| BARNYARDGRASS | 90 | 70 | 50 | 40 | 40 |
| WATERCHESTNUT | 0 | 0 | 0 | 0 | 0 |
| ARROWHEAD | 0 | 0 | 0 | 0 | 0 |
| SCIRPUS | 0 | 0 | 0 | 0 | 0 |
| YELLOW NUTSEDGE | 0 | 0 | 0 | 0 | 0 |
| WATER PLAINTAIN | 0 | 0 | 0 | 0 | 0 |
| RICE JAPONICA EFF | 0 | 0 | 0 | 0 | 0 |
| RICE INDICA EFF | 0 | 0 | 0 | 0 | 0 |
| CMPD 3 | | | | | |
| BARNYARDGRASS | 75 | 50 | 0 | 0 | 0 |
| WATERCHESTNUT | 0 | 0 | 0 | 0 | 0 |
| ARROWHEAD | 0 | 0 | 0 | 0 | 0 |
| SCIRPUS | 0 | 0 | 0 | 0 | 0 |
| YELLOW NUTSEDGE | 0 | 0 | 0 | 0 | 0 |
| WATER PLAINTAIN | 0 | 0 | 0 | 0 | 0 |
| RICE JAPONICA EFF | 0 | 0 | 0 | 0 | 0 |
| RICE INDICA EFF | 0 | 0 | 0 | 0 | 0 |
| CMPD 4 | | | | | |
| BARNYARDGRASS | 100 | 100 | 50 | 50 | 0 |
| WATERCHESTNUT | 0 | 0 | 0 | 0 | 0 |
| ARROWHEAD | 0 | 0 | 0 | 0 | 0 |
| SCIRPUS | 100 | 40 | 0 | 0 | 0 |
| YELLOW NUTSEDGE | 40 | 0 | 0 | 0 | 0 |
| WATER PLAINTAIN | 50 | 0 | 0 | 0 | 0 |
| RICE JAPONICA EFF | 40 | 25 | 0 | 0 | 0 |
| RICE INDICA EFF | 50 | 30 | 20 | 0 | 0 |

What is claimed is:

1. A compound of the formula

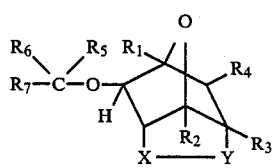

wherein,

X is O, S, NR' or CR'R';
Y is CR"R", C(O), S(O)$_n$ or P(O)(OR$_a$);
n is 1 or 2;
R$_1$ is H or a straight-chain C$_1$-C$_3$ alkyl;
R$_2$ is H, C$_1$-C$_6$ alkyl, C$_2$-C$_4$ alkenyl, C$_2$-C$_4$ alkynyl, phenyl or C$_1$-C$_4$ alkyl substituted by phenyl, OH, CN, OR$_a$, SO$_2$R$_a$, phenyl-SO$_2$, N$_3$, CO$_2$R$_a$, CO$_2$H, OP(O)(OR$_a$)$_2$, P(O)(OR$_a$)$_2$, OC(O)N(R$_a$)$_2$, OC(O)NHR$_a$ or OC(S)N(R$_a$)$_2$;
R$_3$ is H, C$_1$-C$_3$ alkyl, CN, CO$_2$R$_a$, C(O)N(R$_a$)$_2$, C(O)NHR$_a$, C(O)R$_a$, P(O)(OR$_a$)$_2$, CH$_2$OH, CH$_2$OR$_a$, CH$_2$SR$_a$, CH$_2$CN or Cl;
R$_4$ is H, NO$_2$, CO$_2$R$_a$, C(O)NHR$_a$, C(O)N(R$_a$)$_2$, CN or OR$_a$;
R$_5$ is H or F;
R$_6$ is H, F or CH$_3$;
R$_7$ is phenyl optionally substituted with 1-3 substituents selected from W, or J optionally substituted with 1-2 substituents selected from W';

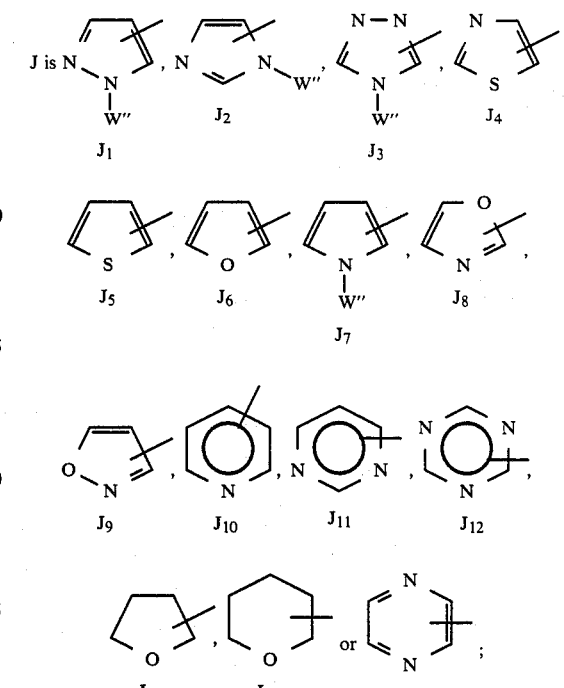

R' is H, C$_1$-C$_3$ alkyl or phenyl;
R" is H or C$_1$-C$_3$ alkyl;
R$_a$ is C$_1$-C$_3$ alkyl;
W is Cl, F, Br, OH, CN, C$_1$-C$_3$ alkyl, C$_1$-C$_3$ haloalkyl, C$_2$-C$_3$ alkenyl, C$_2$-C$_3$ alkynyl, NH$_2$, C(O)NH$_2$, OR$_a$, SR$_a$, NR$_a$H, NR$_a$R$_a$, SOR$_a$, SO$_2$R$_a$, C(O)R$_a$ or CO$_2$R$_a$;
W' is C$_1$-C$_3$ alkyl, F, Cl, Br, C$_1$-C$_2$ alkoxy or C$_1$-C$_2$ alkylthio; and
W" is H or C$_1$-C$_3$ alkyl;
provided that when n is 1 then X is CR'R'.

2. A compound of claim 1 wherein
R$_7$ is phenyl optionally substituted with 1-2 substituents selected from Cl, F, C$_1$-C$_3$ alkyl, OR$_a$, C$_1$-C$_3$ haloalkyl, SR$_a$, C$_2$-C$_3$ alkenyl or C$_2$-C$_3$ alkynyl or J optionally substituted with 1-2 substituents selected from C$_1$-C$_2$ alkyl, F, Cl or OCH$_3$.

3. A compound of claim 2 wherein
R$_1$ is H or C$_1$-C$_2$ alkyl;
R$_2$ is H, C$_1$-C$_2$ alkyl, C$_2$-C$_3$ alkenyl or propargyl; and
R$_3$ is H or C$_1$-C$_2$ alkyl.

4. A compound of claim 3 wherein
X is O; and
Y is CR"R".

5. A compound of claim 3 wherein
X is O; and
Y is C(O).

6. A compound of claim 3 wherein
X is O; and
Y is SO$_2$.

7. A compound of claim 3 wherein
X is O; and
Y is P(O)(OR$_a$).

8. A compound of claim 3 wherein
X is CR'R'; and
Y is CR"R".

9. A compound of claim 3 wherein
X is CR'R'; and

Y is C(O).

10. A compound of claim 3 wherein
X is CR'R'; and
Y is SO or SO$_2$.

11. A compound of claim 3 wherein
X is CR'R'; and
Y is P(O)(OR$_a$).

12. A compound of claim 3 wherein
X is NR'; and
Y is CR"R".

13. A compound of claim 3 wherein
X is NR'; and
Y is C(O).

14. A compound of claim 3 wherein
X is NR'; and
Y is SO$_2$.

15. A compound of claim 3 wherein
X is NR'; and
Y is P(O)(OR$_a$).

16. A compound of claim 3 wherein
X is S; and
Y is CR"R".

17. A compound of claim 3 wherein
X is S; and
Y is C(O).

18. A compound of claim 3 wherein
X is S; and
Y is SO$_2$.

19. A compound of claim 3 wherein
X is S; and
Y is P(O)(OR$_a$).

20. A compound of claim 1 which is
4,8-dioxatricyclo((4.2.1.0$^{3,7}$))nonane-1,5,5,7-tetramethyl-2-(phenylmethoxy).

21. A compound of claim 1 which is
4,8-dioxatricyclo((4.2.1.0$^{3,7}$))nonane-2-(((2-fluorophenyl)-methoxy))-1,5,5,7-tetramethyl.

22. A composition suitable for controlling the growth of undesired vegetation which comprises an effective amount of a compound of claim 1 and at least one of the following: surfactant, solid or liquid diluent.

23. A composition suitable for controlling the growth of undesired vegetation which comprises an effective amount of a compound of claim 2 and at least one of the following: surfactant, solid or liquid diluent.

24. A composition suitable for controlling the growth of undesired vegetation which comprises an effective amount of a compound of claim 3 and at least one of the following: surfactant, solid or liquid diluent.

25. A composition suitable for controlling the growth of undesired vegetation which comprises an effective amount of a compound of claim 20 and at least one of the following: surfactant, solid or liquid diluent.

26. A composition suitable for controlling the growth of undesired vegetation which comprises an effective amount of a compound of claim 21 and at least one of the following: surfactant, solid or liquid diluent.

27. A method for the control of undesired vegetation which comprises applying to the locus to be protected an effective amount of a compound of claim 1.

28. A method for the control of undesired vegetation which comprises applying to the locus to be protected an effective amount of a compound of claim 2.

29. A method for the control of undesired vegetation which comprises applying to the locus to be protected an effective amount of a compound of claim 3.

30. A method for the control of undesired vegetation which comprises applying to the locus to be proected an effective amount of a compound of claim 20.

31. A method for the control of undesired vegetation which comprises applying to the locus to be protected an effective amount of a compound of claim 21.

* * * * *